US012672822B2

(12) United States Patent
Smith et al.

(10) Patent No.: US 12,672,822 B2
(45) Date of Patent: Jul. 7, 2026

(54) THERAPY SCORING FOR HEMODYNAMIC CONDITIONS

(71) Applicant: Becton, Dickinson and Company, Franklin Lakes, NJ (US)

(72) Inventors: Rachel June Smith, Irvine, CA (US); Zhongping Jian, Irvine, CA (US); Feras Al Hatib, Irvine, CA (US); Andrew Marino, Rowland Heights, CA (US); Sai Prasad Buddi, Costa Mesa, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 18/951,241

(22) Filed: Nov. 18, 2024

(65) Prior Publication Data

US 2025/0143637 A1     May 8, 2025

Related U.S. Application Data

(63) Continuation of application No. 16/985,937, filed on Aug. 5, 2020, now Pat. No. 12,144,645.

(Continued)

(51) Int. Cl.
*A61B 5/00*          (2006.01)
*A61B 5/021*          (2006.01)
(Continued)

(52) U.S. Cl.
CPC ............ *A61B 5/4848* (2013.01); *A61B 5/021* (2013.01); *A61B 5/02405* (2013.01);
(Continued)

(58) Field of Classification Search
CPC ... A61B 5/4848; A61B 5/021; A61B 5/02405; A61B 5/029; A61B 5/4839; A61B 5/742; G16H 20/17; G16H 40/67; G16H 50/30
See application file for complete search history.

(56) References Cited

U.S. PATENT DOCUMENTS

| | | | |
|---|---|---|---|
| 5,482,036 A | 1/1996 | Diab et al. | |
| 5,819,226 A | 10/1998 | Gopinathan et al. | |

(Continued)

FOREIGN PATENT DOCUMENTS

| | | | |
|---|---|---|---|
| CN | 1652718 A | 8/2005 | |
| EP | 2679256 A1 | 1/2014 | |

(Continued)

OTHER PUBLICATIONS

Chen, X. et al., Forecasting Acute Hypotensive Episodes in Intensive Care Patients Based on a Peripheral Arterial Blood Pressure Waveform, Computers in Cardiology 2009; 36:545-548.

(Continued)

*Primary Examiner* — Matthew Kremer
*Assistant Examiner* — Nidhi N Patel
(74) *Attorney, Agent, or Firm* — Kinney & Lange, P.A.

(57) ABSTRACT

A system for monitoring arterial pressure of a patient determines a score that is predictive of responsiveness of the patient to a therapy. Sensed hemodynamic data representative of an arterial pressure waveform of the patient are received by a hemodynamic monitor. Magnitude data and trend data are derived from the hemodynamic data. The score that is predictive of the responsiveness of the patient to the therapy is determined based on the magnitude data and the trend data of the hemodynamic parameter. A representation of the score is output.

20 Claims, 22 Drawing Sheets

Related U.S. Application Data

(60) Provisional application No. 62/980,585, filed on Feb. 24, 2020.

(51) Int. Cl.

| | |
|---|---|
| *A61B 5/024* | (2006.01) |
| *A61B 5/029* | (2006.01) |
| *G16H 20/17* | (2018.01) |
| *G16H 40/67* | (2018.01) |
| *G16H 50/30* | (2018.01) |

(52) U.S. Cl.

CPC ............ *A61B 5/029* (2013.01); *A61B 5/4839* (2013.01); *A61B 5/742* (2013.01); *G16H 20/17* (2018.01); *G16H 40/67* (2018.01); *G16H 50/30* (2018.01)

(56) References Cited

U.S. PATENT DOCUMENTS

| | | | |
|---|---|---|---|
| 7,572,230 | B2 | 8/2009 | Neumann et al. |
| 8,478,389 | B1 | 7/2013 | Brockway et al. |
| 9,662,028 | B2 | 5/2017 | Vainoras et al. |
| 2003/0036685 | A1 | 2/2003 | Goodman |
| 2003/0149453 | A1 | 8/2003 | Kroll et al. |
| 2003/0167010 | A1 | 9/2003 | Pinsky |
| 2005/0187796 | A1 | 8/2005 | Rosenfeld et al. |
| 2008/0200775 | A1 | 8/2008 | Lynn |
| 2008/0319332 | A1 | 12/2008 | Sornmo et al. |
| 2011/0077532 | A1 | 3/2011 | Kim et al. |
| 2011/0245631 | A1 | 10/2011 | Genc |
| 2012/0271612 | A1 | 10/2012 | Barsoum et al. |
| 2013/0023776 | A1 | 1/2013 | Olde et al. |
| 2013/0096402 | A1 | 4/2013 | Olde et al. |
| 2013/0204542 | A1 | 8/2013 | Olde et al. |
| 2013/0262357 | A1 | 10/2013 | Amarasingham et al. |
| 2014/0107433 | A1 | 4/2014 | Wegerich |
| 2014/0107504 | A1 | 4/2014 | Stapelfeldt et al. |
| 2014/0279754 | A1 | 9/2014 | Barsoum et al. |
| 2014/0323885 | A1 | 10/2014 | Genc et al. |
| 2014/0364750 | A1 | 12/2014 | Brumfield et al. |
| 2015/0025329 | A1 | 1/2015 | Amarasingham et al. |
| 2015/0065826 | A1 | 3/2015 | Mulligan et al. |
| 2015/0116333 | A1 | 4/2015 | Harper et al. |
| 2015/0150514 | A1 | 6/2015 | Batchinsky et al. |
| 2015/0164437 | A1 | 6/2015 | Mccombie et al. |
| 2015/0282717 | A1 | 10/2015 | Mccombie et al. |
| 2015/0297143 | A1 | 10/2015 | Rajan et al. |
| 2015/0347698 | A1 | 12/2015 | Soni et al. |
| 2016/0012197 | A1 | 1/2016 | Eromo et al. |
| 2016/0142894 | A1 | 5/2016 | Papakonstantinou et al. |
| 2016/0143596 | A1 | 5/2016 | Bhattacharya et al. |
| 2016/0378943 | A1 | 12/2016 | VallÉe |
| 2017/0076211 | A1 | 3/2017 | Kusumura et al. |
| 2017/0116497 | A1 | 4/2017 | Georgescu et al. |
| 2017/0235917 | A1 | 8/2017 | Bighamian et al. |
| 2017/0308981 | A1 | 10/2017 | Razavian et al. |
| 2018/0008205 | A1* | 1/2018 | Al Hatib ............... A61B 5/021 |
| 2018/0020989 | A1 | 1/2018 | Al et al. |
| 2018/0025290 | A1 | 1/2018 | Al Hatib et al. |
| 2018/0028076 | A1* | 2/2018 | Al Hatib ............... G16H 50/30 |
| 2018/0182492 | A1 | 6/2018 | Yamashita |
| 2018/0184901 | A1* | 7/2018 | Akmandor ........... A61B 5/4848 |
| 2018/0322951 | A1 | 11/2018 | Vairavan et al. |
| 2019/0307337 | A1 | 10/2019 | Little et al. |
| 2020/0260965 | A1 | 8/2020 | Munoz et al. |
| 2021/0259629 | A1 | 8/2021 | Smith et al. |
| 2022/0395236 | A1 | 12/2022 | Buddi et al. |
| 2022/0400965 | A1 | 12/2022 | Schneider et al. |
| 2023/0380697 | A1 | 11/2023 | Buddi et al. |

FOREIGN PATENT DOCUMENTS

| | | | | | |
|---|---|---|---|---|---|
| EP | 2730302 | A1 | 5/2014 | | |
| JP | 2006318162 | A | 11/2006 | | |
| JP | 2008506472 | A | 3/2008 | | |
| JP | 2011512929 | A | 4/2011 | | |
| JP | 2014511719 | A | 5/2014 | | |
| JP | 2017060571 | A | 3/2017 | | |
| JP | 2019516477 | A | 6/2019 | | |
| KR | 20090049709 | A | 5/2009 | | |
| WO | 0241771 | A1 | 5/2002 | | |
| WO | WO-2014116276 | A1 * | 7/2014 | ............. | G16H 50/50 |
| WO | WO-2016022989 | A2 * | 2/2016 | ............. | G16H 15/00 |

OTHER PUBLICATIONS

Chiarugi, F., Predicting the Occurrence of Acute Hypotensive Episodes: The PhysioNet Challenge; Computers in Cardiology 2009; 36:621-624.

Communication pursuant to Article 94(3) EPC for European Patent Application No. 21703571.6, dated Apr. 20, 2023, 6 pages.

Communication pursuant to Article 94(3) EPC for European Patent Application No. 21703571.6, dated Dec. 11, 2024, 10 pages.

Communication pursuant to Article 94(3) EPC for European Patent Application No. 21703571.6, dated Feb. 22, 2024, 8 pages.

Communication pursuant to Article 94(3) EPC for European Patent Application No. 21703571.6, dated Oct. 6, 2023, 6 pages.

Fournier, Pa, et al., Acute Hypotension Episode Prediction Using Information Divergence for a Feature Selection, and Non-Parametric Methods for Classification; Computers in Cardiology 2009; 36:625-628.

Hastie, Trevor, Robert Tibshirani, and Jerome Friedman. The elements of statistical learning: data mining, inference, and prediction. Chapters 3 and 11. Springer Science & Business Media, 2009. (Year: 2009).

Hatib F, Jian Z, Buddi S, Lee C, Settels J, Sibert K, Rinehart J, Cannesson M. Machine-learning Algorithm to Predict Hypotension Based on High-fidelity Arterial Pressure Waveform Analysis. Anesthesiology. Oct. 2018; 129(4): 663-674.

Hayn, D., A Biosignal Analysis Applied for Developing an Algorithm Predicting Critical Situations of High Risk Cardiac Patients by Hemodynamic Monitoring; Computers in Cardiology 2009; 36: 629-632.

Henriques, Jh et al., Prediction of Acute Hypotensive Episodes Using Neural Network Multi-models; Computers in Cardiology 2009; 36-549-552.

Ho, Tct et al., Utilizing Histogram to Identify Patients Using Pressors for Acute Hypotension, Computers in Cardiology 2009; 36:797-800.

International Preliminary Report on Patentability for PCT Application No. PCT/US2021/012788, dated Sep. 9, 2022, 10 pages.

International Search Report and Written Opinion for PCT Application No. PCT/US2021/012788, dated May 3, 2021, 11 pages.

Janghorbani et al., "Prediction of Acute Hypotension Episodes Using Logistic Regression Model and Support Vector Machine: A Comparative Study", IEEE, 19th Iranian Conference on Electrical Engineering (Year: 2011).

Jin, K. et al., Smooting and Discriminating MAP Data; Computers in Cardiology 2009; 36: 633-636.

Jousset, F., Computers in Cardiology/Physionet Challenge 2009: Predicting Acute Hypotensive Episodes, 2009; 36:637-640.

Langley, P., et al., Predicting Acute Hypotensive Episodes From Mean Arterial Pressure; Computers in Cardiology 2009; 36: 553-556.

Liu et al., "Utility of Vital Signs, Heart Rate Variability and Complexity, and Machine Learning for Identifying the Need for Lifesaving Interventions in Trauma Patients," SHOCK, vol. 42, No. 2, pp. 108-114, 2014 (Year: 2014).

Maldonado, Sebastian, and Richard Weber. "A wrapper method for feature selection using support vector machines." Information Sciences 179, 13 (2009): 2208-2217. (Year: 2009).

Malik, Marek, et al. "Heart rate variability: Standards of measurement, physiological interpretation, and clinical use." European heartjournal 17.3 (1996): 354-381. (Year: 1996).

Mneimneh, Ma, et al., A Rule-Based Approach for the Prediction of Acute Hypotensive Episodes; Computers in Cardiology 2009; 36: 557-560.

(56) References Cited

OTHER PUBLICATIONS

Moody, GB et al.; Predicting Acute Hypotensive Episodes: The 10th Annual PhysioNet/Computers in Cardiology Challenge, 2009; 36:541-544.

Notice of Reasons for Rejection for Japanese Patent Application No. 2022-550828, dated Dec. 16, 2024, 5 pages.

Notice of Refusal for Japanese Patent Application No. 2022-550828, dated Aug. 26, 2024, 8 pages.

Pinsky, M. R., "Protocolized Cardiovascular Management Based on Ventribular-arterial Coupling," Functional Hemodynamic Monitoring pp. 381-395, Jan. 2005.

Sannino, Giovanna, et al. "To what extent is it possible to predict fails due to standing hypotension by using HRV and wearable devices? Study design and preliminary results from a proof-of-concept study." International Workshop on Ambient Assisted Living. Springer, Cham, 2014. (Year: 2014).

Search Report by Japanese Patent Office for Japanese Patent Application No. 2022-550828, dated Jan. 8, 2021, 29 pages.

First Chinese Office Action for Chinese Patent Application No. 2021800137549, dated Apr. 14, 2026, 16 pages.

* cited by examiner

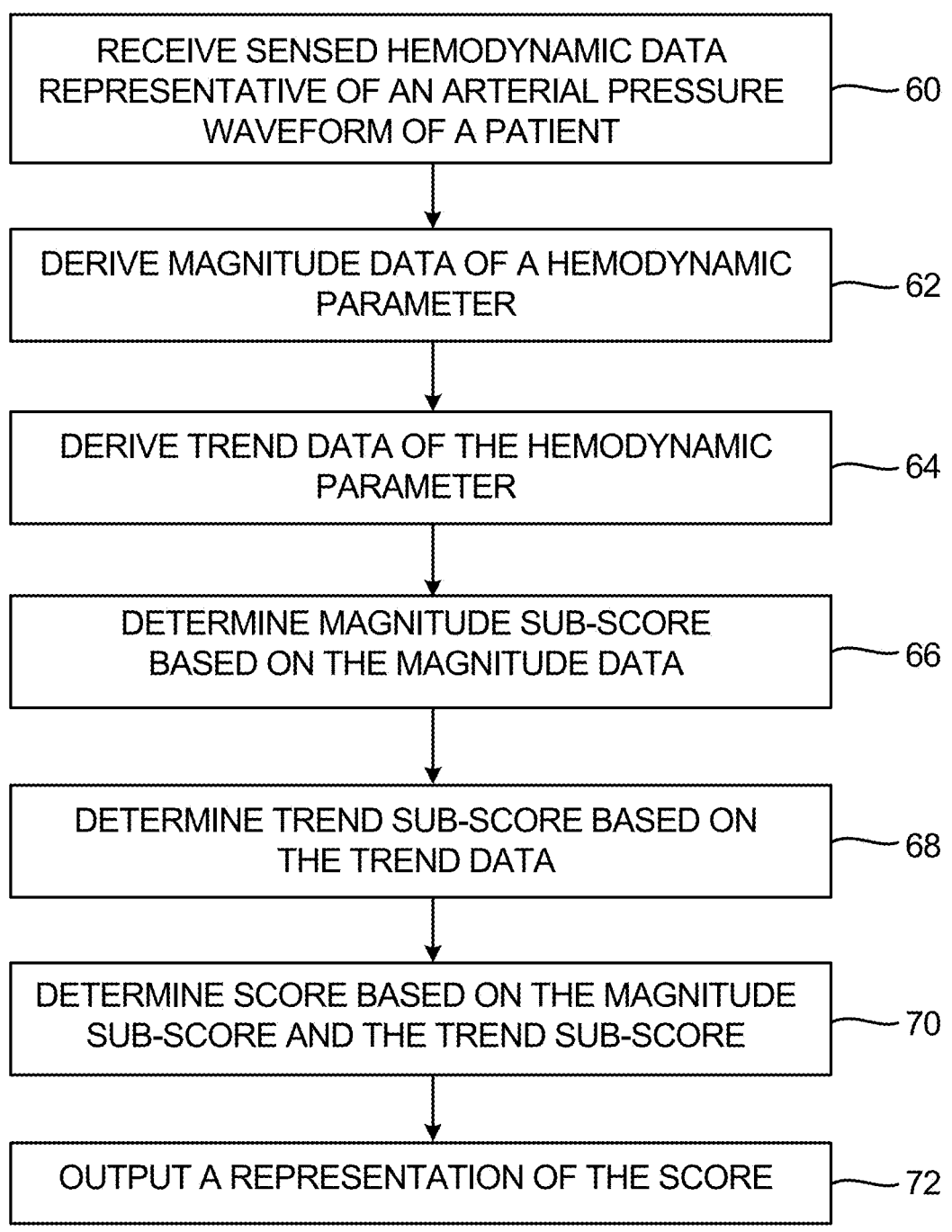

RECEIVE SENSED HEMODYNAMIC DATA REPRESENTATIVE OF AN ARTERIAL PRESSURE WAVEFORM OF A PATIENT — 60

DERIVE MAGNITUDE DATA OF A HEMODYNAMIC PARAMETER — 62

DERIVE TREND DATA OF THE HEMODYNAMIC PARAMETER — 64

DETERMINE MAGNITUDE SUB-SCORE BASED ON THE MAGNITUDE DATA — 66

DETERMINE TREND SUB-SCORE BASED ON THE TREND DATA — 68

DETERMINE SCORE BASED ON THE MAGNITUDE SUB-SCORE AND THE TREND SUB-SCORE — 70

OUTPUT A REPRESENTATION OF THE SCORE — 72

Fig. 5

TherapyScore = AbsoluteScore x TrendScore

Calculate score for individual therapies

FluidScore = AbsoluteFluidScore x FluidTrendscore

FluidScore = AbsoluteFluidScore x FluidTrendScore

Instantaneous
Parameter Value

SVV   <= 7% = 0

SVV   At 8% = 0.16

SVV   At 9% = 0.34

SVV   At 10% = 0.5

SVV   At 11% = 0.66

SVV   At 12% = 0.82

SVV   >= 13% = 1.0

$$FluidScore = AbsoluteFluidScore \times \mathbf{FluidTrendScore}$$

$$e^{\Sigma_{i=1}^{nWindows}(NormSlopeValue)_i * WindowWeight_i}$$

Slope Magnitudes

| I 1 | I 2 | I 3 | I 4 | I 5 |
|-----|-----|-----|------|------|
| +2  | +1.1 | +0.3 | -0.15 | -0.2 |

Normalized Slope Values

| I 1 | I 2 | I 3 | I 4 | I 5 |
|-----|-----|------|------|------|
| +1  | +1  | +0.76 | -0.34 | -0.58 |

Fig. 8K

Normalized Slope Values

| I1 | I2 | I3 | I4 | I5 |
|---|---|---|---|---|
| +1 | +1 | +0.76 | -0.34 | -0.58 |

X

Window Weights

| I1 | I2 | I3 | I4 | I5 |
|---|---|---|---|---|
| 0.3 | 0.2 | 0.1 | 0.05 | 0.02 |

=

| (1)(0.3) | (1)(0.2) | (0.76)(0.1) | (-0.34)(0.05) | (-0.58)(0.02) |
|---|---|---|---|---|

$FluidTrendScore = e^{[0.3+0.2+0.08+(-0.02)+(-0.01)]}$ $FluidTrendScore = e^{0.55} = 1.73$

Fig. 8L

FluidScore = AbsoluteFluidScore x FluidTrendScore

AbsoluteFluidScore = 0.5          (SVV of 10% $\longrightarrow$ 0.5)

FluidTrendScore = 1.73

FluidScore = 0.5 x 1.73 = 0.865 $\longrightarrow$ Fluid Score shows 87

Fluid AbsoluteScore

| SVV (%) | PPV (%) | SVI (ml/m$^2$) | SV (ml) | Assigned Absolute Score |
|---------|---------|----------------|---------|-------------------------|
| >=13    | >=13    | ≤ 30           | ≤ 60    | 1.0                     |
| 11      | 11      | 33             | 66      | 0.67                    |
| 9       | 9       | 37             | 74      | 0.33                    |
| <=7     | <=7     | ≥ 40           | ≥ 80    | 0                       |

Fig. 9A

Inotrope AbsoluteScore

| dP/dt$_{max}$ (mmHg/second) | CO (L /min) | CI (L /min/m$^2$) | Assigned Absolute Score |
|------------------------------|-------------|-------------------|-------------------------|
| <=400                        | ≤ 4         | ≤ 2               | 1.0                     |
| 500                          | 4.6         | 2.3               | 0.67                    |
| 600                          | 5.4         | 2.7               | 0.33                    |
| >=700                        | ≥ 6         | ≥ 3               | 0                       |

Fig. 9B

Vasopressor AbsoluteScore

| SVR (dynes•sec•cm$^{-5}$) | SVRI (dynes•sec•cm$^{-5}$•m$^{2}$) | Assigned Absolute Score |
|---|---|---|
| <= 800 | <= 1600 | 1.0 |
| 900 | 1800 | 0.67 |
| 1000 | 2000 | 0.33 |
| >= 1100 | >= 2200 | 0 |

Fig. 9C

THERAPY SCORING FOR HEMODYNAMIC CONDITIONS

CROSS-REFERENCE TO RELATED APPLICATIONS

This application is a continuation of U.S. application Ser. No. 16/985,937, filed Aug. 5, 2020, and entitled "THERAPY SCORING FOR HEMODYNAMIC CONDITIONS," which claims the benefit of U.S. Provisional Application No. 62/980,585, filed Feb. 24, 2020, the disclosures of which are hereby incorporated by reference in their entirety.

BACKGROUND

The present disclosure relates generally to arterial blood pressure monitoring, and more specifically to the determination of one or more scores, each score being predictive of responsiveness of a patient to a particular therapy.

Arterial blood pressure waveform signals are often utilized in the determination of hemodynamic parameters, such as cardiac output (CO), systemic vascular resistance (SVR), stroke volume (SV), stroke volume variation (SVV), pulse pressure variation (PPV), stroke volume index (SVI), cardiac index (CI), systemic vascular resistance index (SVRI), the maximal rate of rise of arterial pressure (often referred to as $dP/dt_{max}$), or other hemodynamic parameters that can be used to monitor and/or predict important physiological events. Elevated SVV, for example, can indicate a decrease in cardiac preload, which can result in reduced SV, CO, and arterial blood pressure. Similarly, decreased cardiac afterload can be indicated by a decreased SVR, while a decrease in $dP/dt_{max}$ can indicate reduced cardiac contractility. Such conditions, if left untreated, can pose serious risks to surgical patients and critically ill patients, such as impaired organ perfusion, irreversible ischemic damage, neurological deficit, cardiomyopathy, renal impairment, or other serious medical conditions.

Few hospitals are therefore without some form of equipment to monitor one of more of these hemodynamic parameters. For instance, in the operating room during, e.g., a major surgery, an anesthesiologist or other clinician is often tasked with maintaining the mean arterial pressure of a patient to ensure adequate perfusion of organs and peripheral tissues. Attending clinicians will therefore closely monitor such hemodynamic parameters to determine whether administration of a therapeutic agent is indicated.

SUMMARY

In one example, a method for monitoring arterial pressure of a patient and determining a score that is predictive of responsiveness of the patient to a therapy includes receiving, by a hemodynamic monitor, sensed hemodynamic data representative of an arterial pressure waveform of the patient. The method further includes deriving, by the hemodynamic monitor from the hemodynamic data, magnitude data and trend data of a hemodynamic parameter, and determining, by the hemodynamic monitor, the score that is predictive of the responsiveness of the patient to the therapy based on the magnitude data and the trend data of the hemodynamic parameter. The method further includes outputting, by the hemodynamic monitor, a representation of the score.

In another example, a system for monitoring arterial pressure of a patient and determining a score that is predictive of responsiveness of the patient to a therapy includes a hemodynamic sensor, a system memory, a user interface, and a hardware processor. The hemodynamic sensor produces hemodynamic data representative of an arterial pressure waveform of the patient. The system memory stores hemodynamic therapy scoring software code. The hardware processor is configured to execute the hemodynamic therapy scoring software code to derive, from the hemodynamic data representative of the arterial pressure waveform of the patient, magnitude data and trend data of a hemodynamic parameter. The hardware processor is further configured to execute the hemodynamic therapy scoring software code to determine the score that is predictive of the responsiveness of the patient to the therapy based on the magnitude data and the trend data of the hemodynamic parameter, and output a representation of the score via the user interface.

BRIEF DESCRIPTION OF THE DRAWINGS

FIG. 5 is a flow diagram illustrating example operations for determining at least one score that is predictive of responsiveness of a patient to a therapy.

FIG. 8K is a chart illustrating an example for normalizing slopes of the best-fit lines used for determining the trend sub-score of the fluid therapy score.

FIG. 8L is a chart illustrating an example for applying weights to the normalized slopes of the best-fit lines and aggregating the weighted normalized slopes to determine the trend sub-score of the fluid therapy score.

FIG. 9A is a chart illustrating further examples for determining a magnitude sub-score associated with therapeutic intravenous delivery of fluid to the patient.

FIG. 9B is a chart illustrating examples for determining a magnitude sub-score associated with therapeutic intravenous delivery of an inotrope to the patient.

FIG. 9C is a chart illustrating examples for determining a magnitude sub-score associated with therapeutic intravenous delivery of a vasopressor to the patient.

DETAILED DESCRIPTION

As described herein, a hemodynamic monitoring system determines one or more scores that are predictive of responsiveness of a patient to a corresponding therapy, thereby providing one or more quantitative metrics that can improve decision support for medical personnel in delivering timely and effective therapeutic interventions. The hemodynamic monitoring system, implementing techniques of this disclosure, determines the one or more scores as a combination of magnitude data and trend data derived from a corresponding hemodynamic parameter. Accordingly, the one or more scores are determined based on both a value of a corresponding hemodynamic parameter and trends of the hemodynamic parameter over, e.g., time, to more accurately predict both current and future responsiveness of the patient to a corresponding therapy.

Figure 1:
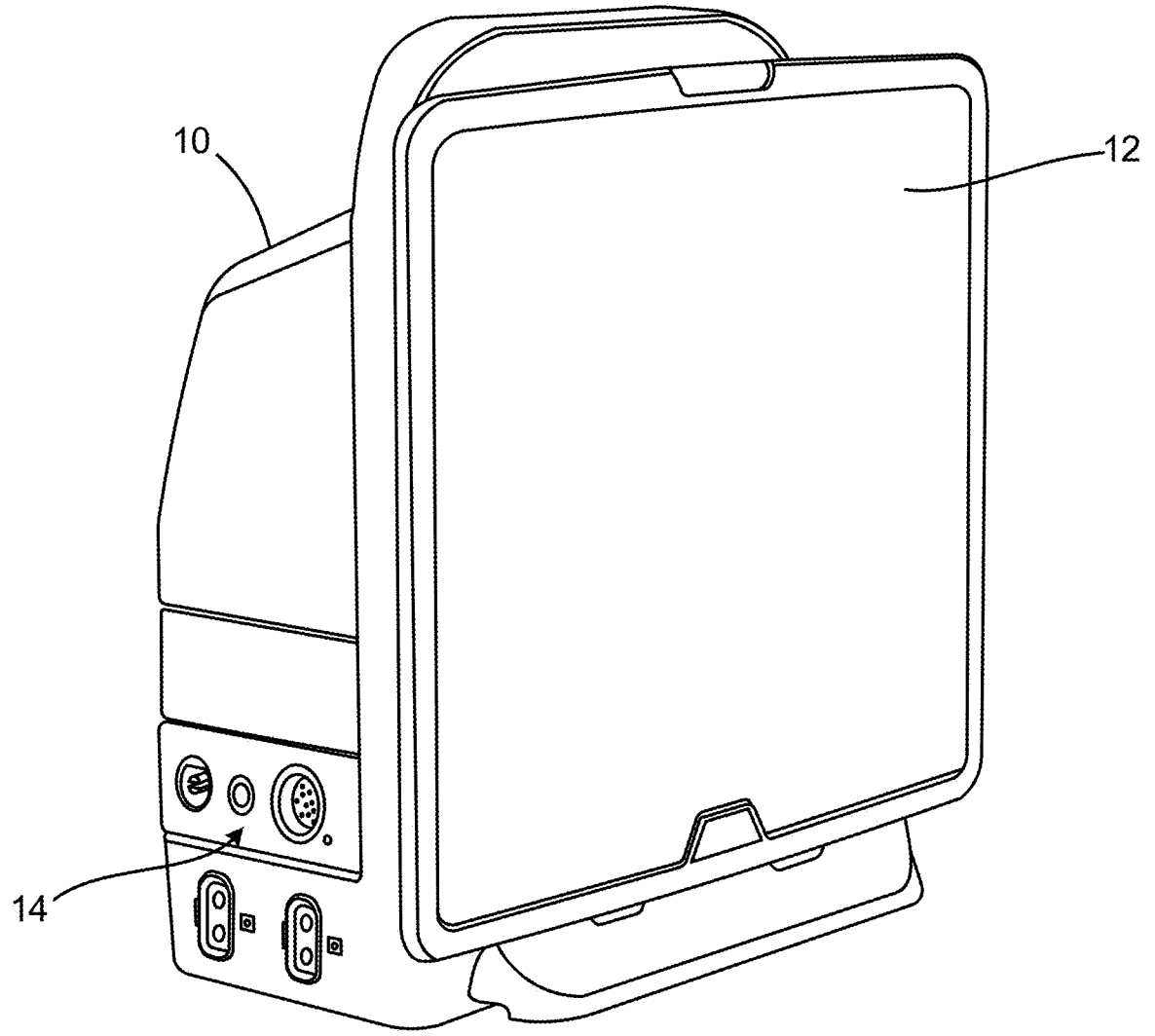
FIG. 1 is a perspective view of an example hemodynamic monitor that determines at least one score that is predictive of responsiveness of a patient to a therapy.

FIG. 1 is a perspective view of hemodynamic monitor 10 that determines at least one score that is predictive of responsiveness of a patient to a therapy. As illustrated in FIG. 1, hemodynamic monitor 10 includes display 12 that can present a graphical user interface including control elements (e.g., graphical control elements) that enable user interaction with hemodynamic monitor 10, as well as output display elements for presenting information to a user, such as at least one score that is predictive of responsiveness of the patient to a corresponding therapy. Hemodynamic monitor 10 can also include a plurality of input and/or output (I/O) connectors configured for wired connection (e.g., electrical and/or communicative connection) with one or more peripheral components, such as one or more hemodynamic sensors, as is further described below. For instance, as illustrated in FIG. 1, hemodynamic monitor 10 can include I/O connectors 14. While the example of FIG. 1 illustrates five separate I/O connectors 14, it should be understood that in other examples, hemodynamic monitor 10 can include fewer than five I/O connectors or greater than five I/O connectors. In yet other examples, hemodynamic monitor 10 may not include I/O connectors 14, but rather may communicate wirelessly with various peripheral devices.

As is further described below, hemodynamic monitor 10 includes one or more processors and computer-readable memory that stores hemodynamic therapy scoring software code. Hemodynamic therapy scoring code is executable to produce at least one score that is predictive of responsiveness of a patient to a therapy. For example, hemodynamic monitor 10 can receive sensed hemodynamic data representative of an arterial pressure waveform of the patient, such as via one or more hemodynamic sensors connected to hemodynamic monitor 10 via I/O connectors 14. Hemodynamic monitor 10 executes the hemodynamic therapy scoring software code to derive at least one hemodynamic parameter that can indicate an underlying hemodynamic condition of the patient. For instance, decreased cardiac preload, which can result in reduced stroke volume, cardiac output, arterial blood pressure, and impaired organ perfusion, can be indicated by an elevated stroke volume variation (SVV), and can be treatable by therapeutic delivery (e.g., intravenous delivery) of fluids, such as saline fluids. Decreased cardiac afterload, which can result in hypotension and potential impairment of organ perfusion, can be indicated by a decreased systemic vascular resistance (SVR), and can be treatable by therapeutic delivery of a vasopressor (i.e., a vasoconstrictor). Decreased cardiac contractility, which can result in reduced ventricular ejection, cardiac output, arterial blood pressure, and impaired organ perfusion, can be indicated by a decreased maximal rate of rise of arterial pressure (often referred to as $dP/dt_{max}$), and can be treatable by therapeutic delivery of an inotrope.

Hemodynamic monitor 10 executes the hemodynamic therapy scoring software code to determine the one or more scores that are predictive of responsiveness of the patient to a corresponding therapy. The one or more scores can include, e.g., a fluid therapy score indicative of decreased cardiac preload and predictive of responsiveness of the patient to therapeutic delivery of fluids (indicated by, e.g., an elevated SVV), a vasopressor therapy score indicative of decreased cardiac afterload and predictive of responsiveness of the patient to therapeutic delivery of a vasopressor (indicated by, e.g., a decreased SVR), an inotrope therapy score indicative of decreased cardiac contractility and predictive of responsiveness of the patient to therapeutic delivery of an inotrope (indicated by, e.g., a decreased $dP/dt_{max}$), or other scores.

As is further described below, hemodynamic monitor 10 can determine the one or more scores as a combination of magnitude data and trend data derived from the corresponding hemodynamic parameter. Accordingly, hemodynamic monitor 10 can determine the one or more scores based on both a value of the corresponding hemodynamic parameter and one or more trends of the hemodynamic parameter over, e.g., time, to more accurately predict responsiveness of the patient to a corresponding therapy. Hemodynamic monitor 10 further executes the hemodynamic therapy scoring software code to output a representation (or representations) of the one or more scores. For example, as is further described below, the representation of a score can include the display of the score at, e.g., display 12 of hemodynamic monitor 10, a color coding of the score, a symbolic representation of the score, an audible representation of the score, or other representations of the score.

As such, hemodynamic monitor 10, implementing techniques of this disclosure, can provide one or more scores that are predictive of responsiveness of a patient to a corresponding therapy to assist clinicians or other medical personnel with determinations of timely and effective therapeutic treatments for indicated hemodynamic conditions while decreasing the information processing burden on clinicians during, e.g., surgery or other clinical events.

Figure 2:
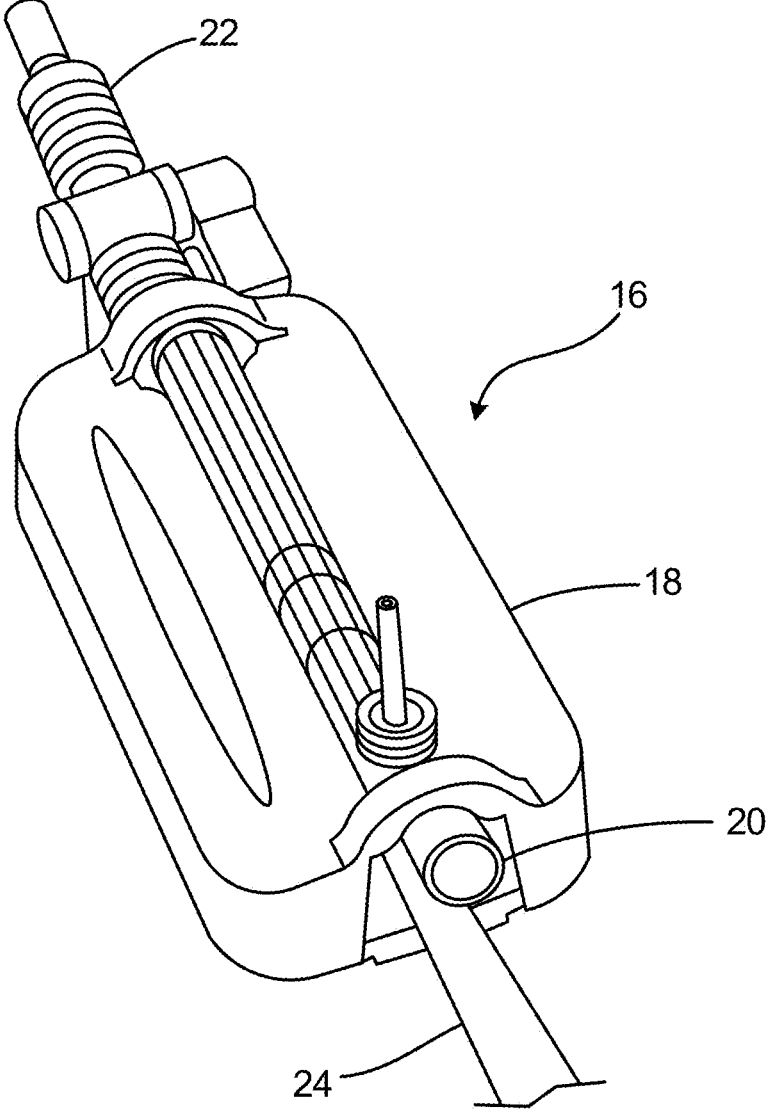
FIG. 2 is a perspective view of an example minimally invasive pressure sensor for sensing hemodynamic data representative of arterial pressure of a patient.

FIG. 2 is a perspective view of hemodynamic sensor 16 that can be attached to a patient for sensing hemodynamic data representative of arterial pressure of the patient. Hemodynamic sensor 16, illustrated in FIG. 2, is one example of a minimally invasive hemodynamic sensor that can be attached to the patient via, e.g., a radial arterial catheter inserted into an arm of the patient. In other examples, hemodynamic sensor 16 can be attached to the patient via a femoral arterial catheter inserted into a leg of the patient.

As illustrated in FIG. 2, hemodynamic sensor 16 includes housing 18, fluid input port 20, catheter-side fluid port 22, and I/O cable 24. Fluid input port 20 is configured to be connected via tubing or other hydraulic connection to a fluid source, such as a saline bag or other fluid input source. Catheter-side fluid port 22 is configured to be connected via tubing or other hydraulic connection to a catheter (e.g., a radial arterial catheter or a femoral arterial catheter) that is inserted into an arm of the patient (i.e., a radial arterial catheter) or a leg of the patient (i.e., a femoral arterial catheter). I/O cable 24 is configured to connect to hemodynamic monitor 10 via, e.g., one or more of I/O connectors 14 (FIG. 1). Housing 18 of hemodynamic sensor 16 encloses one or more pressure transducers, communication circuitry, processing circuitry, and corresponding electronic components to sense fluid pressure corresponding to arterial pressure of the patient that is transmitted to hemodynamic monitor 10 (FIG. 1) via I/O cable 24.

In operation, a column of fluid (e.g., saline solution) is introduced from a fluid source (e.g., a saline bag) through hemodynamic sensor 16 via fluid input port 20 to catheter-side fluid port 22 toward the catheter inserted into the patient. Arterial pressure is communicated through the fluid column to pressure sensors located within housing 16 which sense the pressure of the fluid column. Hemodynamic sensor 16 translates the sensed pressure of the fluid column to an electrical signal via the pressure transducers and outputs the corresponding electrical signal to hemodynamic monitor 10 (FIG. 1) via I/O cable 24. Hemodynamic sensor 16 therefore transmits analog sensor data (or a digital representation of the analog sensor data) to hemodynamic monitor 10 (FIG. 1) that is representative of substantially continuous beat-to-beat monitoring of the arterial pressure of the patient.

Figure 3:
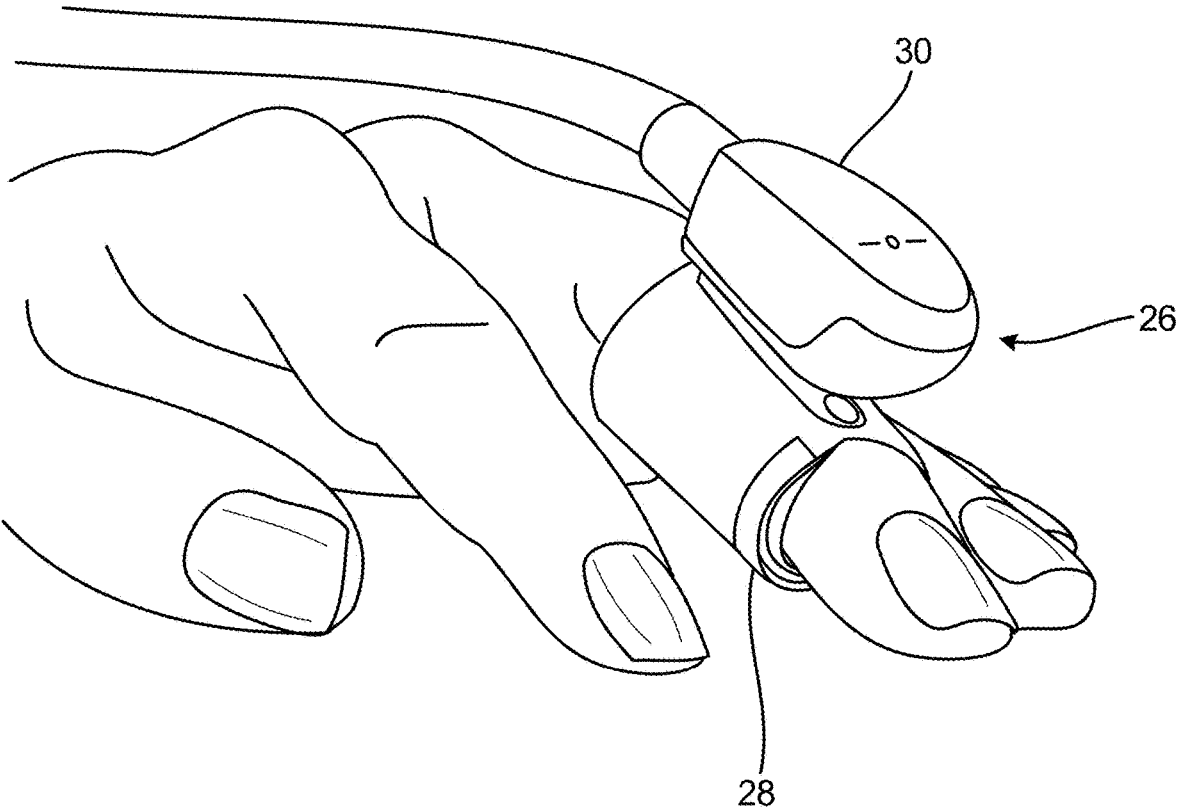
FIG. 3 is a perspective view of an example non-invasive sensor for sensing hemodynamic data representative of arterial pressure of a patient.

FIG. 3 is a perspective view of hemodynamic sensor 26 for sensing hemodynamic data representative of arterial pressure of a patient. Hemodynamic sensor 26, illustrated in FIG. 3, is one example of a non-invasive hemodynamic sensor that can be attached to the patient via one or more finger cuffs to sense data representative of arterial pressure of the patient. As illustrated in FIG. 3, hemodynamic sensor 26 includes inflatable finger cuff 28 and heart reference sensor 30. Inflatable finger cuff 28 includes an inflatable blood pressure bladder configured to inflate and deflate as controlled by a pressure controller (not illustrated) that is pneumatically connected to inflatable finger cuff 28. Inflatable finger cuff 28 also includes an optical (e.g., infrared) transmitter and an optical receiver that are electrically connected to heart reference sensor 30 to measure the changing volume of the arteries in the finger.

In operation, the pressure controller continually adjusts pressure within the finger cuff to maintain a constant volume of the arteries in the finger (i.e., the unloaded volume of the arteries) as measured by heart reference sensor 30 via the optical transmitter and optical receiver of inflatable finger cuff 28. The pressure applied by the pressure controller to continuously maintain the unloaded volume is representative of the blood pressure in the finger, and is communicated by the pressure controller to heart reference sensor 30. Heart reference sensor 30 translates the pressure signal representative of the blood pressure in the finger to hemodynamic data representative of the arterial pressure waveform of the patient, which is transmitted to hemodynamic monitor 10 (FIG. 1) via, e.g., I/O connectors 14 (FIG. 1). Accordingly, hemodynamic sensor 26 transmits sensor data that is representative of substantially continuous beat-to-beat monitoring of the arterial pressure of the patient.

Figure 4:
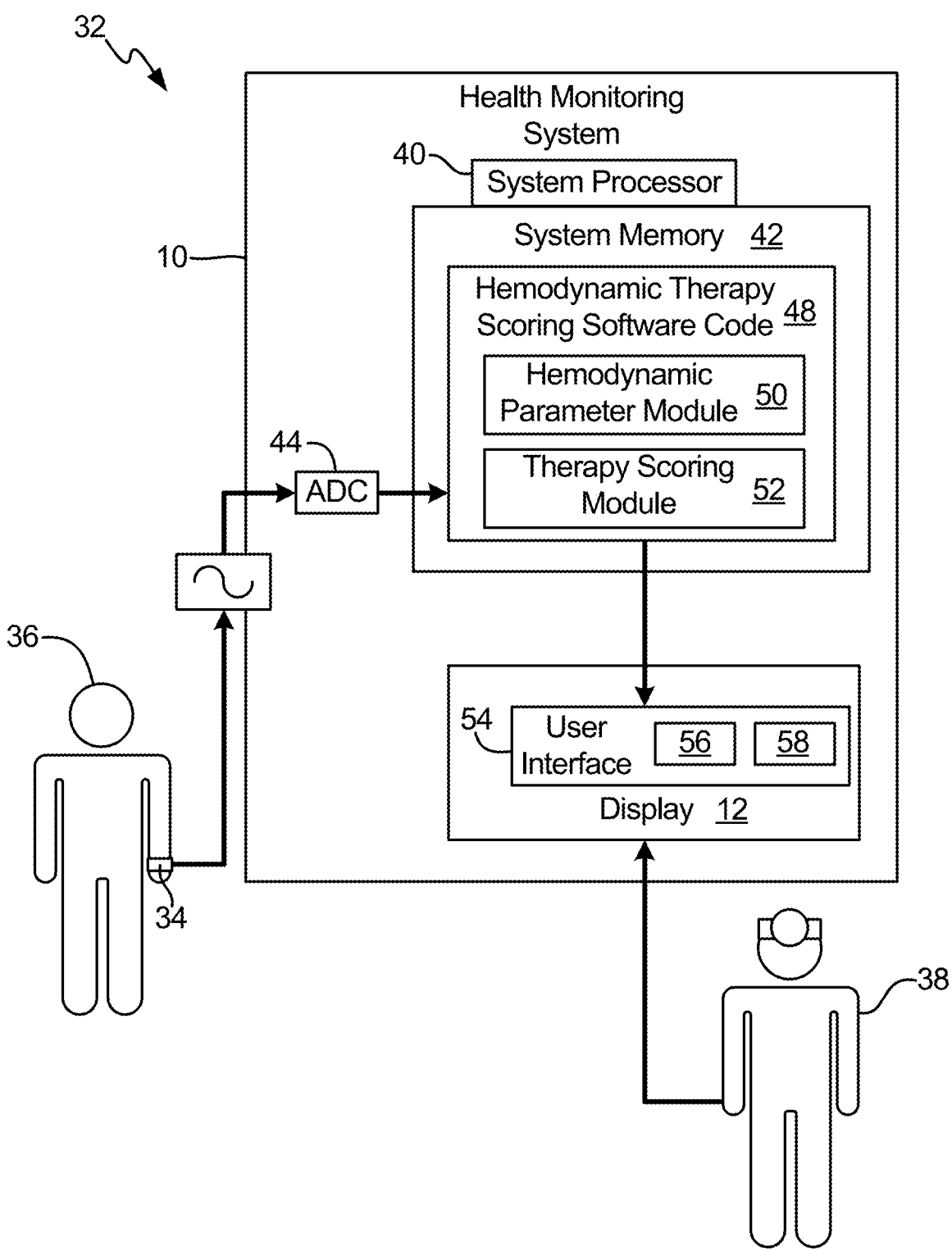
FIG. 4 is a block diagram illustrating an example hemodynamic monitoring system that determines at least one score that is predictive of responsiveness of a patient to a therapy.

FIG. 4 is a block diagram of hemodynamic monitoring system 32 that determines one or more scores that are predictive of responsiveness of a patient to a corresponding therapy. As illustrated in FIG. 4, hemodynamic monitoring system 32 includes hemodynamic monitor 10 and hemodynamic sensor 34. Hemodynamic monitoring system 32 can be implemented within a patient care environment, such as an ICU, an OR, or other patient care environment. As illustrated in FIG. 4, the patient care environment can include patient 36 and healthcare worker 38 trained to utilize hemodynamic monitoring system 32.

Hemodynamic monitor 10, as described above with respect to FIG. 1, can be, e.g., an integrated hardware unit including system processor 40, system memory 42, display 12, and analog-to-digital (ADC) converter 44. In other examples, any one or more components and/or described functionality of hemodynamic monitor 10 can be distributed among multiple hardware units. For instance, in some examples, display 12 can be a separate display device that is remote from and operatively coupled with hemodynamic monitor 10. In general, though illustrated and described in the example of FIG. 4 as an integrated hardware unit, it should be understood that hemodynamic monitor 10 can include any combination of devices and components that are electrically, communicatively, or otherwise operatively connected to perform functionality attributed herein to hemodynamic monitor 10.

As illustrated in FIG. 4, system memory 42 stores hemodynamic therapy scoring software code 48. Hemodynamic therapy scoring software code 48 includes hemodynamic parameter module 50 and therapy scoring module 52. Display 12 provides user interface 54, which includes control elements 56 that enable user interaction with hemodynamic monitor 10 and/or other components of hemodynamic monitoring system 32. User interface 54, as illustrated in FIG. 4, can also provide graphical and/or audible outputs 58 that display or otherwise present medical personnel (e.g., healthcare worker 38) with the one or more scores predictive of responsiveness of patient 36 to corresponding therapies.

Hemodynamic sensor 34 can be attached to patient 36 to sense hemodynamic data representative of an arterial pressure waveform of patient 36. Hemodynamic sensor 34 is operatively connected to hemodynamic monitor 10 (e.g., electrically and/or communicatively connected via wired or wireless connection, or both) to provide the sensed hemodynamic data to hemodynamic monitor 10. In some examples, hemodynamic sensor 34 provides the hemodynamic data representative of the arterial pressure waveform of patient 36 to hemodynamic monitor 10 as an analog signal, which is converted by ADC 44 to digital hemodynamic data representative of the arterial pressure waveform. In other examples, hemodynamic sensor 34 can provide the sensed hemodynamic data to hemodynamic monitor 10 in digital form, in which case hemodynamic monitor 10 may not include or utilize ADC 44. In yet other examples, hemodynamic sensor 34 can provide the hemodynamic data representative of the arterial pressure waveform of patient 36 to hemodynamic monitor 10 as an analog signal, which is analyzed in its analog form by hemodynamic monitor 10.

Hemodynamic sensor 34 can be a non-invasive or minimally invasive sensor attached to patient 36. For instance, hemodynamic sensor 34 can take the form of minimally invasive hemodynamic sensor 16 (FIG. 2), non-invasive hemodynamic sensor 26 (FIG. 3), or other minimally invasive or non-invasive hemodynamic sensor. In some examples, hemodynamic sensor 34 can be attached non-invasively at an extremity of patient 36, such as a wrist, an arm, a finger, an ankle, a toe, or other extremity of patient 36. As such, hemodynamic sensor 34 can take the form of a small, lightweight, and comfortable hemodynamic sensor suitable for extended wear by patient 36 to provide substantially continuous beat-to-beat monitoring of the arterial pressure of patient 36 over an extended period of time, such as minutes or hours.

In certain examples, hemodynamic sensor 34 can be configured to sense an arterial pressure of patient 36 in a minimally invasive manner. For instance, hemodynamic sensor 34 can be attached to patient 36 via a radial arterial catheter inserted into an arm of patient 36. In other examples, hemodynamic sensor 34 can be attached to patient 36 via a femoral arterial catheter inserted into a leg of patient 36. Such minimally invasive techniques can similarly enable hemodynamic sensor 34 to provide substantially continuous beat-to-beat monitoring of the arterial pressure of patient 36 over an extended period of time, such as minutes or hours.

System processor 40 is configured to execute hemodynamic therapy scoring software code 48, which implements hemodynamic parameter model 50 and therapy scoring module 52 to produce one or more scores that are predictive of responsiveness of patient 36 to a corresponding therapy. Examples of system processor 40 can include any one or more of a microprocessor, a controller, a digital signal processor (DSP), an application specific integrated circuit (ASIC), a field-programmable gate array (FPGA), or other equivalent discrete or integrated logic circuitry.

System memory 42 can be configured to store information within hemodynamic monitor 10 during operation. System memory 42, in some examples, is described as computer-readable storage media. In some examples, a computer-readable storage medium can include a non-transitory medium. The term "non-transitory" can indicate that the storage medium is not embodied in a carrier wave or a propagated signal. In certain examples, a non-transitory storage medium can store data that can, over time, change (e.g., in RAM or cache). System memory 42 can include volatile and non-volatile computer-readable memories. Examples of volatile memories can include random access memories (RAM), dynamic random access memories (DRAM), static random access memories (SRAM), and other forms of volatile memories. Examples of non-volatile memories can include, e.g., magnetic hard discs, optical discs, flash memories, or forms of electrically programmable memories (EPROM) or electrically erasable and programmable (EEPROM) memories.

Display 12 can be a liquid crystal display (LCD), a light-emitting diode (LED) display, an organic light-emitting diode (OLED) display, or other display device suitable for providing information to users in graphical form. User interface 54 can include graphical and/or physical control elements that enable user input to interact with hemodynamic monitor 10 and/or other components of hemodynamic monitoring system 32. In some examples, user interface 54 can take the form of a graphical user interface (GUI) that presents graphical control elements presented at, e.g., a touch-sensitive and/or presence sensitive display screen of display 12. In such examples, user input can be received in the form of gesture input, such as touch gestures, scroll gestures, zoom gestures, or other gesture input. In certain examples, user interface 54 can take the form of and/or include physical control elements, such as physical buttons, keys, knobs, or other physical control elements configured to receive user input to interact with components of hemodynamic monitoring system 32.

Operation of hemodynamic monitoring system 32 to produce one or more risk scores that are predictive of responsiveness of patient 36 to a corresponding therapy is described further below in combination with the flow diagram of FIG. 5. As illustrated in FIG. 5, hemodynamic monitor 10 receives sensed hemodynamic data representative of an arterial pressure waveform of patient 36 (Step 60).

For example, hemodynamic sensor 34 can sense hemodynamic data representative of an arterial pressure waveform of patient 36. Hemodynamic sensor 34 can provide the hemodynamic data (e.g., as analog sensor data) to hemodynamic monitor 10. ADC 44 can convert the analog hemodynamic data to digital hemodynamic data representative of the arterial pressure waveform of patient 36.

Hemodynamic monitor 10 derives magnitude data of a hemodynamic parameter from the hemodynamic data representative of the arterial pressure waveform of patient 36 (Step 62). For instance, as is further described below, hemodynamic monitor 10 can execute hemodynamic therapy scoring software code 48 to implement hemodynamic parameter module 50 to derive hemodynamic parameter data from the arterial pressure waveform data. Such hemodynamic parameter data can include, e.g., any one or more of SVV data, SVR data, $dP/dt_{max}$ data, or other hemodynamic parameter data. Magnitude data of the one or more hemodynamic parameters can take the form of, e.g., derived values of the hemodynamic parameters over time. For example, as described above, elevated SVV can indicate a decreased cardiac preload, which can be treatable by therapeutic delivery of fluids. Hemodynamic parameter module 50 can derive time-varying SVV magnitude data from the hemodynamic data representative of the arterial pressure waveform of patient 36, such SVV magnitude data being usable to determine a score that is predictive of responsiveness of patient 36 to therapeutic delivery of fluids, such as saline fluid. Similarly, hemodynamic parameter module 50 can derive time-varying SVR magnitude data that is usable to determine a score that is predictive of responsiveness of patient 36 to therapeutic delivery of a vasopressor, such as norepinephrine, dopamine and epinephrine, or other vasoconstrictors. Hemodynamic parameter module 50 can derive time-varying $dP/dt_{max}$ magnitude data that is usable to determine a score that is predictive of responsiveness of patient 36 to therapeutic delivery of an inotrope, such as dobutamine, milrinone, amrinone, calcium sensitizing agents, or other inotropic drugs.

Hemodynamic monitor 10 derives trend data of the hemodynamic parameter (Step 64). For example, hemodynamic monitor 10 can execute hemodynamic therapy scoring software code 48 to implement hemodynamic parameter module 50 to derive trend data of the hemodynamic parameter. Such trend data can take the form of, e.g., a best-fit line (or a plurality of best-fit lines) of the hemodynamic parameter data associated with one or more defined time intervals, as is further described below. Hemodynamic parameter module 50 can derive any one or more of SVV trend data (or PPV trend data, or SV trend data, or SVI trend data) that is usable to determine the score that is predictive of responsiveness of patient 36 to therapeutic delivery of fluids, SVR trend data (or SVRI trend data) that is usable to determine the score that is predictive of responsiveness of patient 36 to therapeutic delivery of a vasopressor, and $dP/dt_{max}$ trend data (or CI trend data, or CO trend data) that is usable to determine the score that is predictive of responsiveness of patient 36 to therapeutic delivery of an inotrope.

Hemodynamic monitor 10 determines a magnitude sub-score based on the derived magnitude data of the hemodynamic parameter (Step 66). For instance, as is further described below, hemodynamic monitor 10 can execute hemodynamic therapy scoring software code 48 to implement therapy scoring module 52 to determine a magnitude sub-score as a normalized value ranging between a lower normalized threshold (e.g., a lower threshold numerical value of zero) at a lower magnitude threshold of the magnitude data and an upper normalized threshold (e.g., an upper threshold numerical value of one) at an upper magnitude threshold of the magnitude data. The lower and upper magnitude thresholds of the magnitude data can be a function of the hemodynamic parameter. For instance, as is further described below, the lower magnitude threshold for SVV parameter data can be 7% (e.g., corresponding to a lower normalized numerical threshold of zero), and the upper magnitude threshold for SVV parameter data can be 13% (e.g., corresponding to an upper normalized numerical threshold of one). Therapy scoring module 52 can determine a magnitude sub-score (e.g., as a normalized value) for any one or more of SVV parameter data, SVR parameter data, and dP/dt$_{max}$ parameter data.

Hemodynamic monitor 10 determines a trend sub-score based on the derived trend data of the hemodynamic parameter (Step 68). For example, as is further described below, hemodynamic monitor 10 can execute hemodynamic therapy scoring software code 48 to implement therapy scoring module 52 to determine a trend sub-score as an aggregation of one or more weighted (and, in some examples, normalized) best-fit lines associated with one or more defined time intervals of the hemodynamic parameter data. Therapy scoring module 52 can determine the trend sub-score for any one or more of SVV parameter data, PPV parameter data, SV parameter data, SVI parameter data, SVR parameter data, SVRI parameter data, CI parameter data, CI parameter data, and dP/dt$_{max}$ parameter data.

Hemodynamic monitor 10 determines one or more scores based on the magnitude sub-score and an associated trend sub-score, each score being predictive of responsiveness of patient 36 to a corresponding therapy (Step 70). For example, hemodynamic monitor 10 can execute hemodynamic therapy scoring software code 48 to implement therapy scoring module 52 to determine the one or more scores as a combination of the magnitude sub-score and the associated trend sub-score, such as a multiplicative product of the magnitude sub-score and the trend-sub score.

Hemodynamic monitor 10 outputs a representation of each of the one or more scores (Step 72). For instance, as is further described below, hemodynamic monitor 10 can output any one or more of a numerical representation of each score, a color-coded numerical representation of each score, a symbolic representation of each score, an audible representation of each score, or other representation (or representations) of each score (e.g., via display 12, one or more speaker devices, or other output devices).

Accordingly, hemodynamic monitor 10, implementing techniques of this disclosure, provides one or more scores that are predictive of responsiveness of patient 36 to a corresponding therapy, thereby reducing the information processing burden on attending medical personnel and providing decision support to such medical personnel for timely and effective delivery of therapeutic treatments for indicated hemodynamic conditions. Moreover, the provided scores, which are determined from not only magnitude data but also from trend data of the derived hemodynamic parameters, can help to indicate the future responsiveness of the patient to the corresponding therapy, thereby further enhancing the decision support provided by the corresponding scores.

Figure 6:
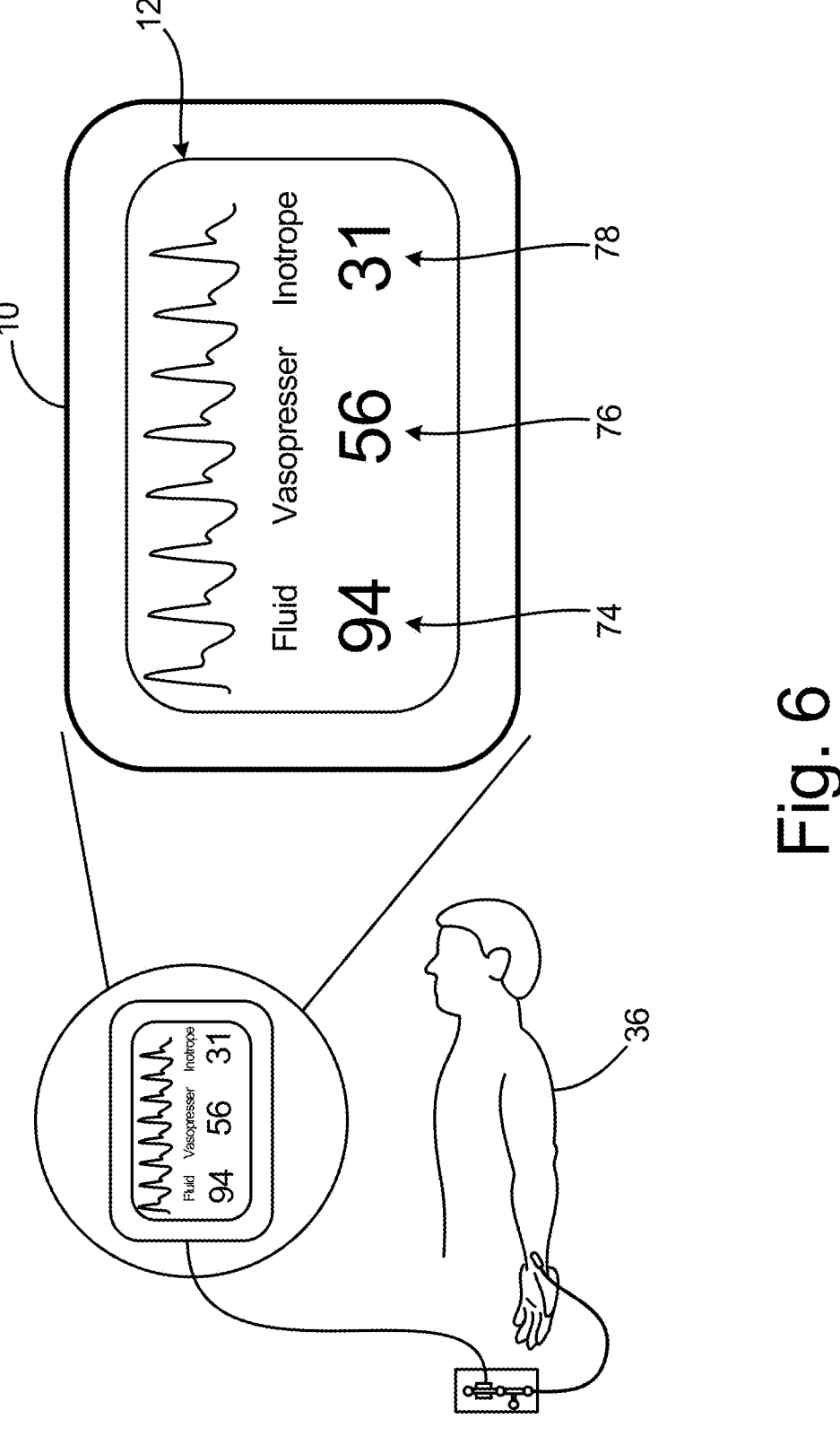
FIG. 6 is a block diagram illustrating an example of a hemodynamic monitor displaying three separate scores, each score being predictive of responsiveness of a patient to a respective therapy.

FIG. 6 is a block diagram illustrating a further example of hemodynamic monitor 10 displaying three separate scores that are each predictive of responsiveness of patient 36 to a respective therapy. As illustrated in FIG. 6, hemodynamic monitor 10 displays, at display 12, fluid score 74, vasopressor score 76, and inotrope score 78. Fluid score 74 (having a value of "94" in the example of FIG. 6) represents a score determined by hemodynamic monitor 10 based on SVV (or PPV, or SVI, or SV) parameter data and predictive of responsiveness of patient 36 to therapeutic delivery of fluids. Vasopressor score 76 (having a value of "56" in the example of FIG. 6) represents a score determined by hemodynamic monitor 10 based on SVR parameter data and predictive of responsiveness of patient 36 to therapeutic delivery of a vasopressor. Inotrope score 78 (having a value of "31" in the example of FIG. 6) represents a score determined by hemodynamic monitor 10 based on dP/dt$_{max}$ parameter data (or CO parameter data, or CI parameter data), and predictive of responsiveness of patient 36 to therapeutic delivery of an inotrope. While the example of FIG. 6 illustrates and describes three separate scores (74, 76, and 78), it should be understood that in other examples, hemodynamic monitor 10 can determine and provide (e.g., display) any one or more of fluid score 74, vasopressor score 76, and inotrope score 78.

As illustrated in FIG. 6, each of fluid score 74, vasopressor score 76, and inotrope score 78 has a value that ranges between a lower numerical threshold value of zero and an upper numerical threshold value of one hundred. In other examples, hemodynamic monitor 10 can determine and/or provide scores 74, 76, and 78 as numerical values ranging between other lower and upper numerical threshold values, such as between a value of zero and one, between a value of negative one and one, between a value of zero and ten, or any other defined ranges. Similarly, though in the example of FIG. 6, the upper numerical threshold value (e.g., one hundred) corresponds to a prediction of high responsiveness to the corresponding therapy and the lower numerical threshold (e.g., zero) corresponds to a prediction of low responsiveness to the corresponding therapy, in other examples, such correspondence of predicted responsiveness to the lower and upper numerical thresholds can be reversed (e.g., a lower threshold corresponding to a prediction of high responsiveness and an upper threshold corresponding to a prediction of low responsiveness).

In some examples, hemodynamic monitor 10 can display scores 74, 76, and 78 as color-coded scores based on a value of the respective score. For instance, hemodynamic monitor 10 can display fluid score 74 as a first color (e.g., green) in response to determining that fluid score 74 is within a first range of values corresponding to a low predicted responsiveness of patient 36 to therapeutic delivery of fluid (e.g., between a value of zero and a value of forty, or other ranges). Similarly, hemodynamic monitor 10 can display fluid score 74 as a second color (e.g., yellow) in response to determining that fluid score 74 is within a second range of values corresponding to a moderate predicted responsiveness of patient 36 to therapeutic delivery of fluid (e.g., between a value of forty and a value of eighty, or other ranges). Hemodynamic monitor 10 can display fluid score 74 as a third color (e.g., red) in response to determining that fluid score 74 is within a third range of values corresponding to a high predicted responsiveness of patient 36 to therapeutic delivery of fluid (e.g., between a value of eighty and a value of one hundred, or other ranges). It should be understood that the example ranges described herein (i.e., a first range of zero to forty, a second range of forty to eighty, and a third range of eighty to one hundred) are merely illustrative, and can be different ranges (and, in some examples, adjustable) depending on a desired sensitivity of the score to graphically display the predicted responsiveness of the patient to the corresponding therapy.

In some examples, hemodynamic monitor 10 can invoke a sensory alarm in response to determining that any one or more of scores 74, 76, and 78 satisfy threshold alarming criteria, such as criteria that indicate a high predicted responsiveness of patient 36 to a corresponding therapy (e.g., a value greater than eighty, or other threshold criteria). The sensory alarm can take the form of a visual alarm, an audible alarm, a haptic alarm, or other type of sensory alarm. For instance, the sensory alarm can be invoked as any combination of flashing and/or colored graphics shown by display 12, a warning sound such as a siren or repeated tone, a haptic alarm configured to cause hemodynamic monitor 10 to vibrate or otherwise deliver a physical impulse perceptible to an attending healthcare worker or other user, or other type of sensory alarm.

Accordingly, hemodynamic monitor 10 can provide one or more scores to indicate to clinicians or other medical personnel both the presence of a therapy (or therapies) to which a patient is predicted to respond and the identity of the such therapy (or therapies). As such, hemodynamic monitor 10 can facilitate attending medical personnel in the decision to timely and effectively provide therapeutic treatment to stabilize or prevent an underlying hemodynamic condition of the patient.

Figure 7:
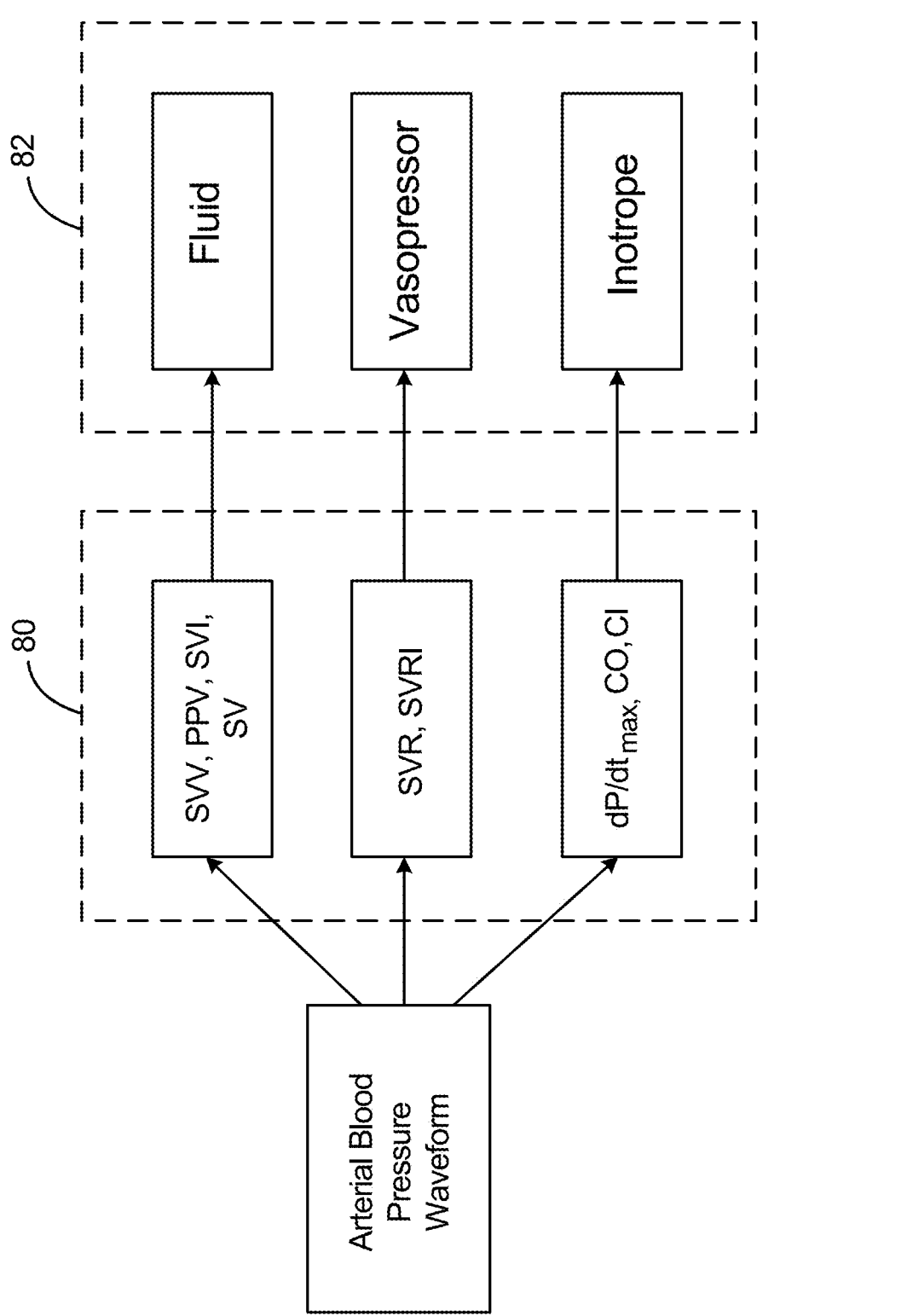
FIG. 7 is a chart illustrating a relationship between hemodynamic parameters derived from an arterial pressure waveform and corresponding therapies.

FIG. 7 is a chart illustrating a relationship between hemodynamic parameters 80 and corresponding therapies 82. As illustrated in FIG. 7, hemodynamic parameters 80 can include, among others, SVV, PPV, SVI, SV, SVR, SVRI, dP/dt$_{max}$, CO, and CI. Therapies 82 can include, among others, therapeutic delivery of fluids, a vasopressor, and an inotrope. As illustrated in FIG. 7, and as described above, an elevated SVV and/or PPV (or a decreased SVI or SV) can indicate decreased cardiac preload, which can be treatable by the corresponding therapeutic delivery of fluids to a patient. Decreased SVR and/or SVRI can indicate decreased cardiac afterload, which can be treatable by the corresponding therapeutic delivery of a vasopressor to the patient. Decreased dP/dt$_{max}$, CO, and/or CI can indicate decreased cardiac contractility, which can be treatable by the corresponding therapeutic delivery of an inotrope to the patient.

FIGS. 8A-8M illustrate an example of hemodynamic monitor 10 (FIGS. 1, 4 and 6) to determine a fluid therapy score that is predictive of responsiveness of a patient to the therapeutic delivery of fluids. Though the examples of FIGS. 8A-8M are described below with respect to a fluid therapy score, it should be understood that the examples of FIGS. 8A-8M are applicable to other therapy scores, such as a vasopressor therapy score that is predictive of responsiveness of the patient to therapeutic delivery of a vasopressor and an inotrope therapy score that is predictive of responsiveness of the patient to therapeutic delivery of an inotrope. Moreover, though the examples of FIGS. 8A-8M are described below with respect to a fluid therapy score that is based on SVV parameter data, it should be understood that the examples of FIGS. 8A-8M are applicable to the determination of the fluid therapy score that is based on any one or more of SVV, PPV, SVI, and SV parameter data.

Figure 8A:
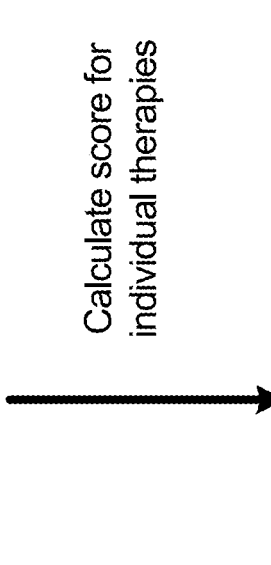
FIG. 8A is a chart illustrating an example for determining a fluid therapy score associated with therapeutic intravenous delivery of fluid to a patient.

As illustrated in FIG. 8A, hemodynamic monitor 10 can determine a score that is predictive of responsiveness of a patient to a corresponding therapy as a combination of (e.g., a multiplicative product of) a magnitude sub-score (illustrated in FIG. 8A as "AbsoluteScore") and a trend sub-score (illustrated in FIG. 8A as "TrendScore") that is determined based on magnitude data and trend data of a hemodynamic parameter. Hemodynamic monitor 10 can determine any one or more scores that are predictive of responsiveness of the patient to any one or more corresponding therapies. In the example of FIG. 8A, hemodynamic monitor 10 determines a fluid therapy score (illustrated in FIG. 8A as "FluidScore")

as the multiplicative product of a fluid magnitude sub-score (illustrated in FIG. 8A as "AbsoluteFluidScore") and a fluid trend sub-score (illustrated in FIG. 8A as "FluidTrendScore").

Figure 8B:
FIG. 8B is a chart illustrating an example for determining a magnitude sub-score of the fluid therapy score associated with the therapeutic intravenous delivery of fluid to the patient.

FIG. 8B illustrates an example for determining the fluid magnitude sub-score of FIG. 8A, which is illustrated in FIG. 8B as "AbsoluteFluidScore." As illustrated in FIG. 8B, hemodynamic monitor 10 can determine the fluid magnitude sub-score as a normalized value ranging between a lower normalized threshold having a numerical value of zero at a lower magnitude threshold of 7% SVV and an upper normalized threshold having a numerical value of one at an upper magnitude threshold of 13%, though other normalized value thresholds and magnitude thresholds are possible.

In the example of FIG. 8B, hemodynamic monitor 10 linearly interpolates between the lower normalized threshold and the upper normalized threshold to determine the fluid magnitude sub-score for those intermediate SVV values that are greater than the lower magnitude threshold (e.g., 7% in the example of FIG. 8B) and lower than the upper magnitude threshold (e.g., 13% in the example of FIG. 8B). In other examples, hemodynamic monitor 10 need not linearly interpolate, but rather can determine fluid magnitude sub-scores for intermediate SVV values based on a non-linear interpolation. Hemodynamic monitor 10, as is further described below, utilizes the fluid magnitude sub-score for determining the fluid score that is predictive of responsiveness of the patient to therapeutic delivery of fluids.

Figure 8C:
FIG. 8C is a chart illustrating an example for determining a trend sub-score of the fluid score associated with the therapeutic intravenous delivery of fluid to the patient.

FIG. 8C illustrates an example for determining the fluid trend sub-score of FIG. 8A. As illustrated in FIG. 8C, hemodynamic monitor 10 can determine the fluid trend sub-score (illustrated in FIG. 8C as "FluidTrendScore") based on an aggregation of normalized slopes of best-fit lines of the hemodynamic parameter (SVV in this example, which corresponds to therapeutic delivery of fluids) associated with one or more defined time intervals. For example, hemodynamic monitor 10 can determine the fluid trend sub-score according to the following equation:

$$FluidTrendScore = e^{\sum_{i=1}^{nWindows}(NormSlopeValue)_i*(WindowWeight)_i} \quad \text{(Equation 1)}$$

where nWindows is the number of defined time intervals, NormSlopeValue is the normalized slope of the best-fit line of the hemodynamic parameter associated with the corresponding defined time interval, and WindowWeight is a weighting value associated with the corresponding time interval.

Figure 8D:
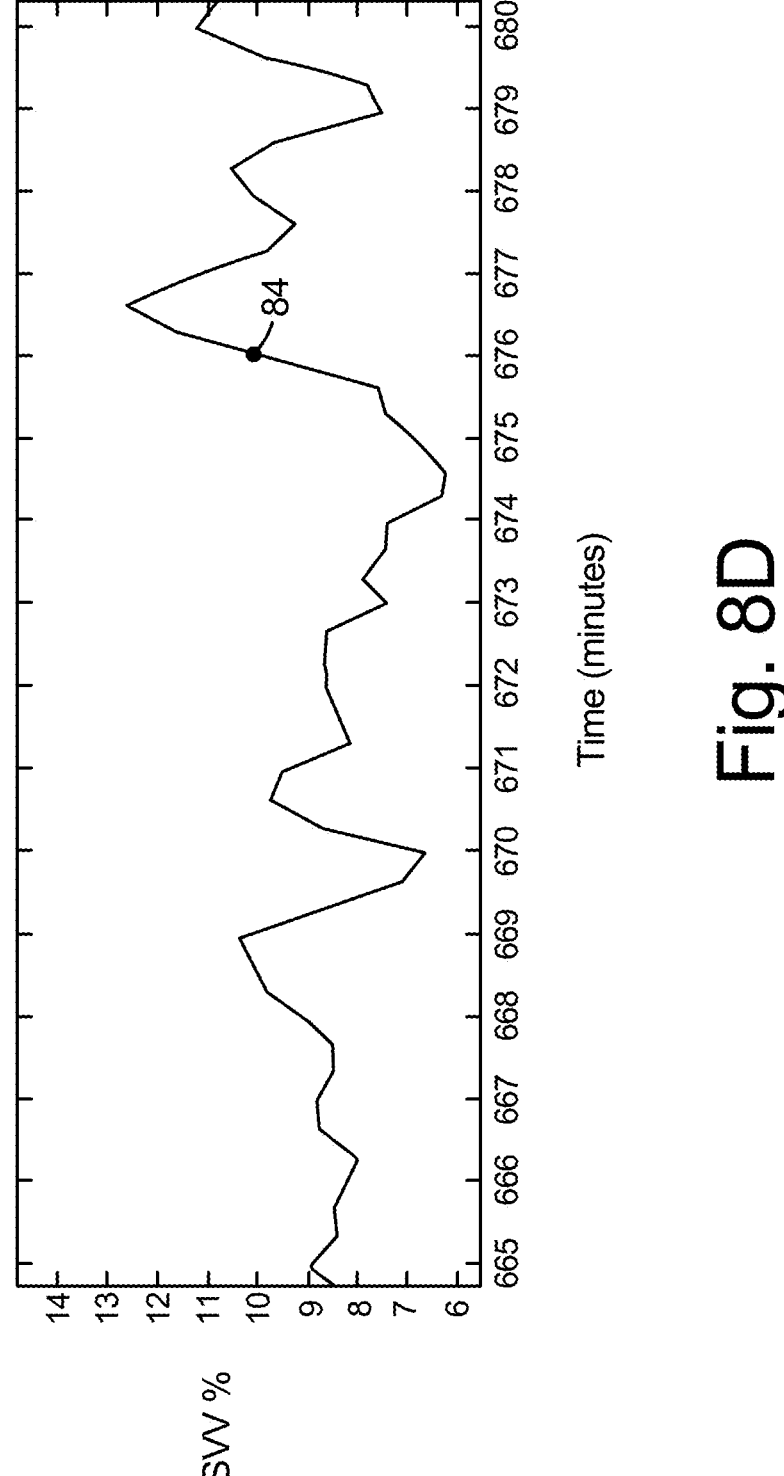
FIGS. 8D-8J are graphs of stroke volume variation (SVV) of the patient versus time that illustrate examples of best-fit lines for defined time intervals that are used for determining the trend sub-score of the fluid therapy score.

FIGS. 8D-8J illustrate an example for determining trend data using a best-fit line associated with five defined time intervals of SVV parameter data. FIG. 8D illustrates a graph of example SVV parameter data plotted as a percentage of SVV as a function of time in minutes. As illustrated in FIG. 8D, hemodynamic monitor 10 can evaluate the SVV parameter using initial evaluation point 84. In the example of FIG. 8D, initial evaluation point 84 corresponds to the percentage of SVV (10% SVV) at a time of 676 minutes. Though in the example of FIG. 8D initial evaluation point 84 is taken at minute 676, which is not the most current time for which SVV data is available, it should be understood that initial evaluation point 84 can be taken at any time for which SVV data is available. For instance, in certain examples, the initial evaluation point can be determined as the most current time for which the hemodynamic parameter data (SVV in this example) is available, such that the example operations of FIGS. 8D-8J are performed on an iterative basis as new hemodynamic parameter data becomes available.

Figure 8E:
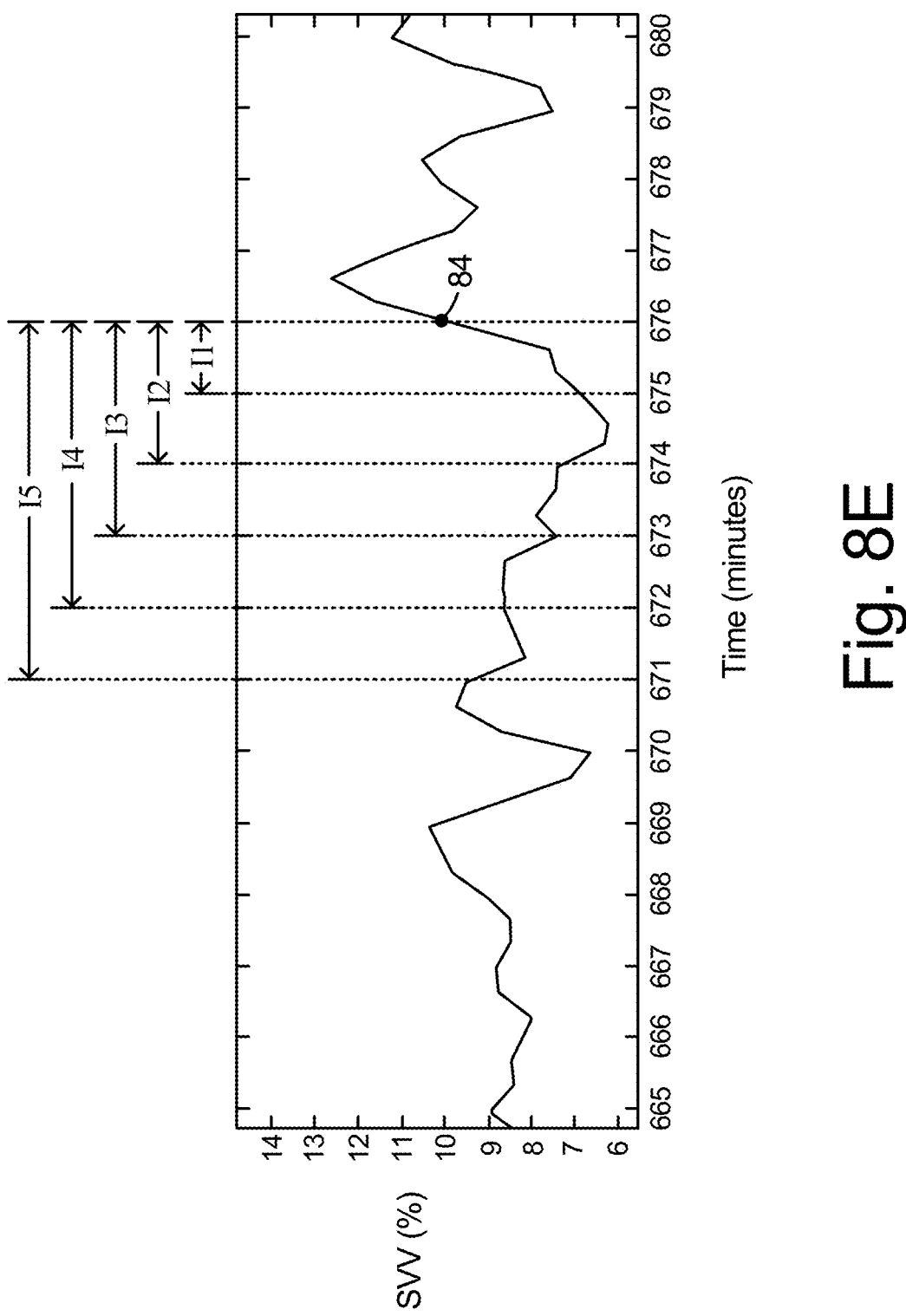

FIG. 8E illustrates a graph of the SVV parameter data, and shows a plurality of defined time intervals of the SVV data. In particular, the example of FIG. 8E illustrates five separate time intervals, namely interval I1 that includes SVV data for a previous minute of data (i.e., with respect to minute 676 corresponding to initial evaluation point 84) and including SVV data from minute 675 to minute 676, interval 12 that includes SVV data for a previous two minutes of data and including SVV data from minute 674 to minute 676, interval 13 that includes SVV data for a previous three minutes of data and including SVV data from minute 673 to minute 676, interval 14 that includes SVV data for a previous four minutes of data and including SVV data from minute 672 to minute 676, and interval 15 that includes SVV data for a previous five minutes of data and including SVV data from minute 671 to minute 676.

While the example of FIG. 8E illustrates five separate time intervals (I1-I5), in other examples, hemodynamic monitor 10 can utilize any one or more time intervals. For instance, in some examples, hemodynamic monitor 10 can utilize a single defined time interval for deriving trend data of the hemodynamic parameter (e.g., SVV). In other examples, hemodynamic monitor 10 can utilize two, three, four, five, or more defined time intervals for deriving the trend data. In addition, though the example of FIG. 8E illustrates the use of time intervals that have a duration of integer numbers of minutes, hemodynamic monitor 10 need not utilize integer numbers of minutes in all examples. For instance, hemodynamic monitor 10 can derive the trend data of the hemodynamic parameter using defined time intervals of ten seconds, fifteen seconds, thirty seconds, ninety seconds, or time intervals having any other non-integer number of minutes (or seconds).

Figure 8F:
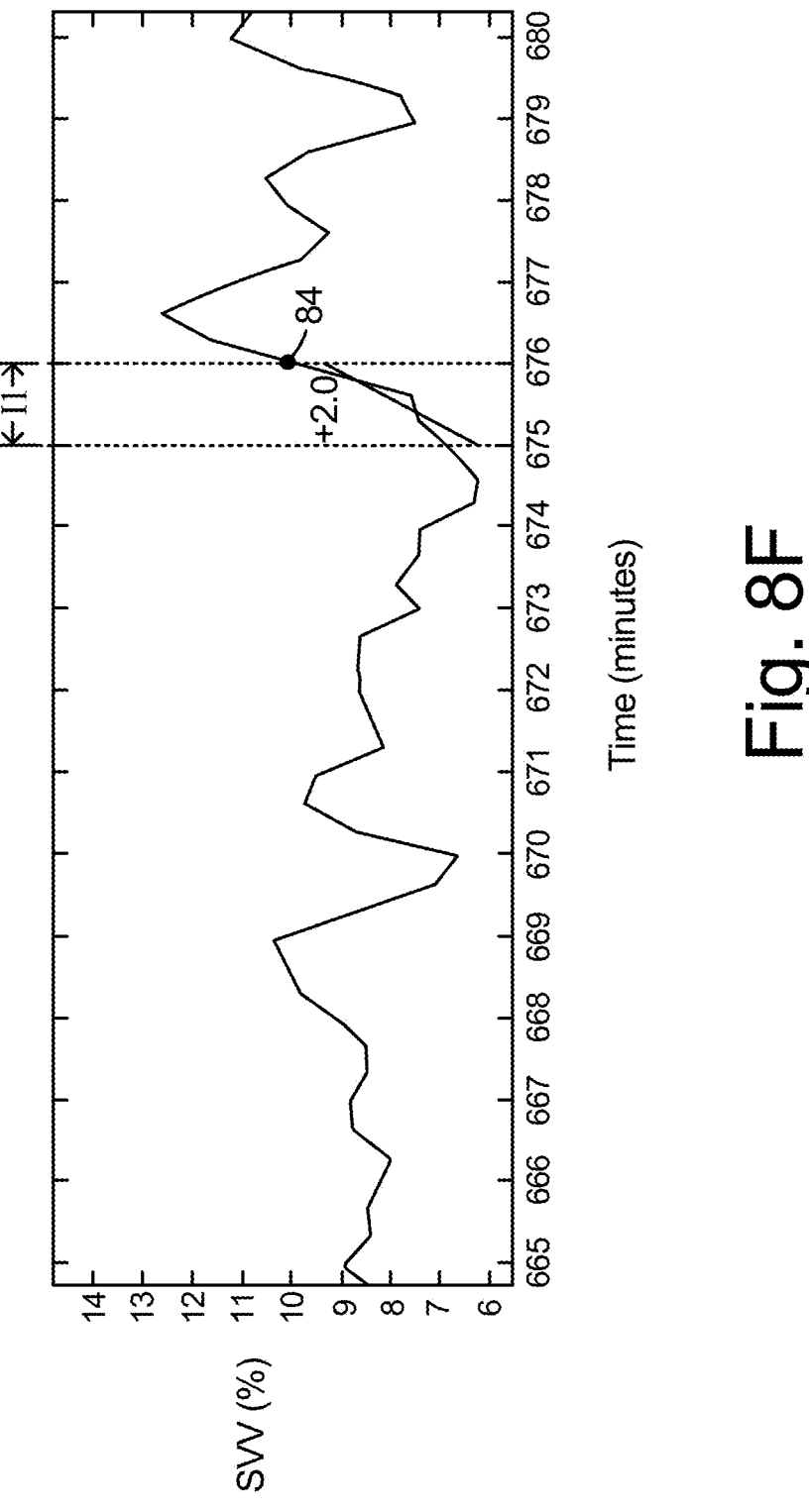
Figure 8G:
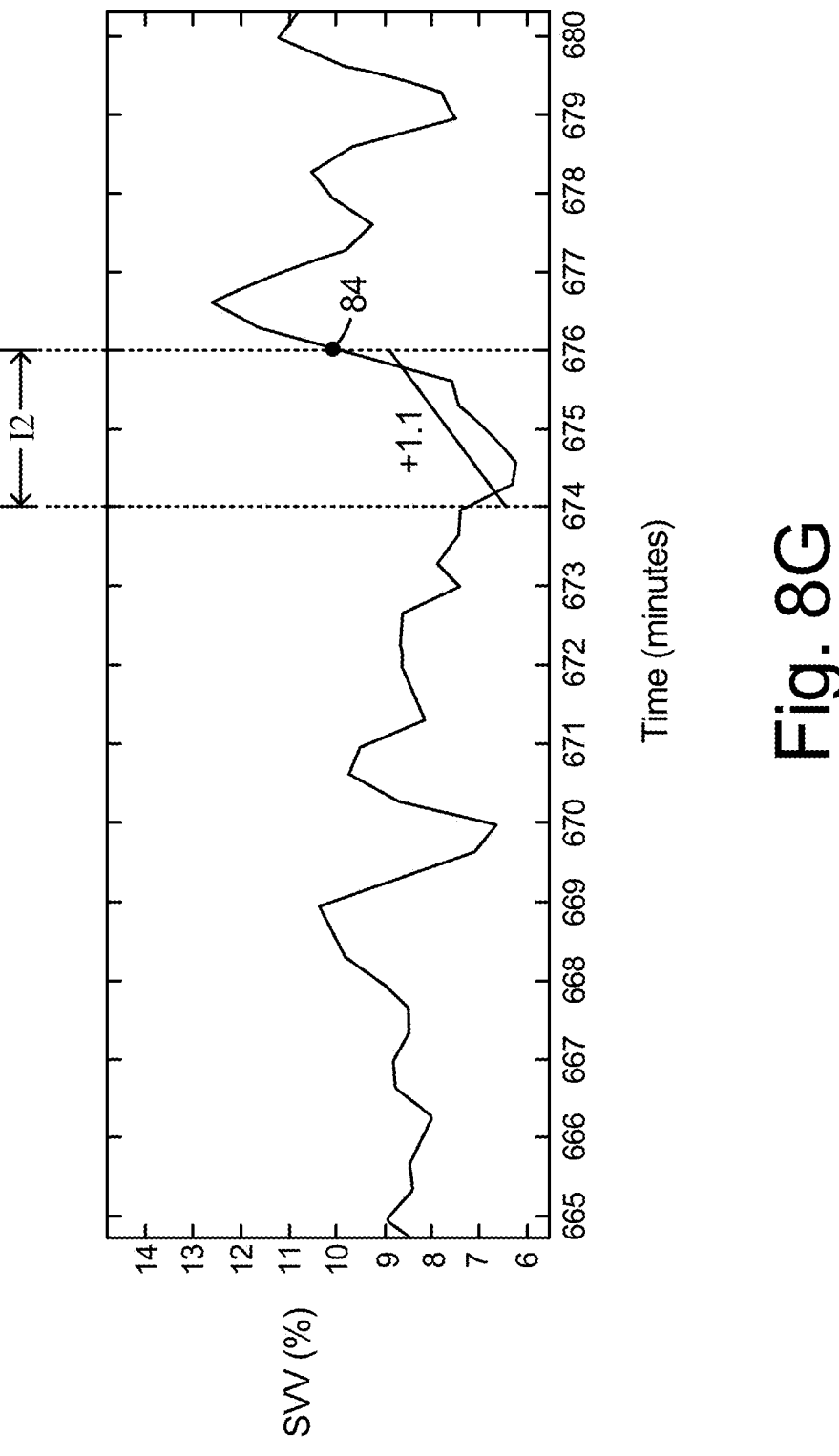

FIG. 8F illustrates an example of hemodynamic monitor 10 to determine the trend data of SVV for time interval I1. As illustrated in FIG. 8F, hemodynamic monitor 10 can determine trend data for SVV using the SVV data included in time interval I1 (e.g., a previous one minute of SVV data) as a slope of a best-fit line through the SVV data included in interval I1 using, e.g., a linear regression, though other linear or non-linear trend determinations are possible, such as by using a polynomial trend line, an exponential trend line, or other trend determinations. In the example of FIG. 8F, hemodynamic monitor 10 determines a slope of a best-fit line through the SVV data included in interval I1 as having a numerical value of positive two.

Figure 8H:
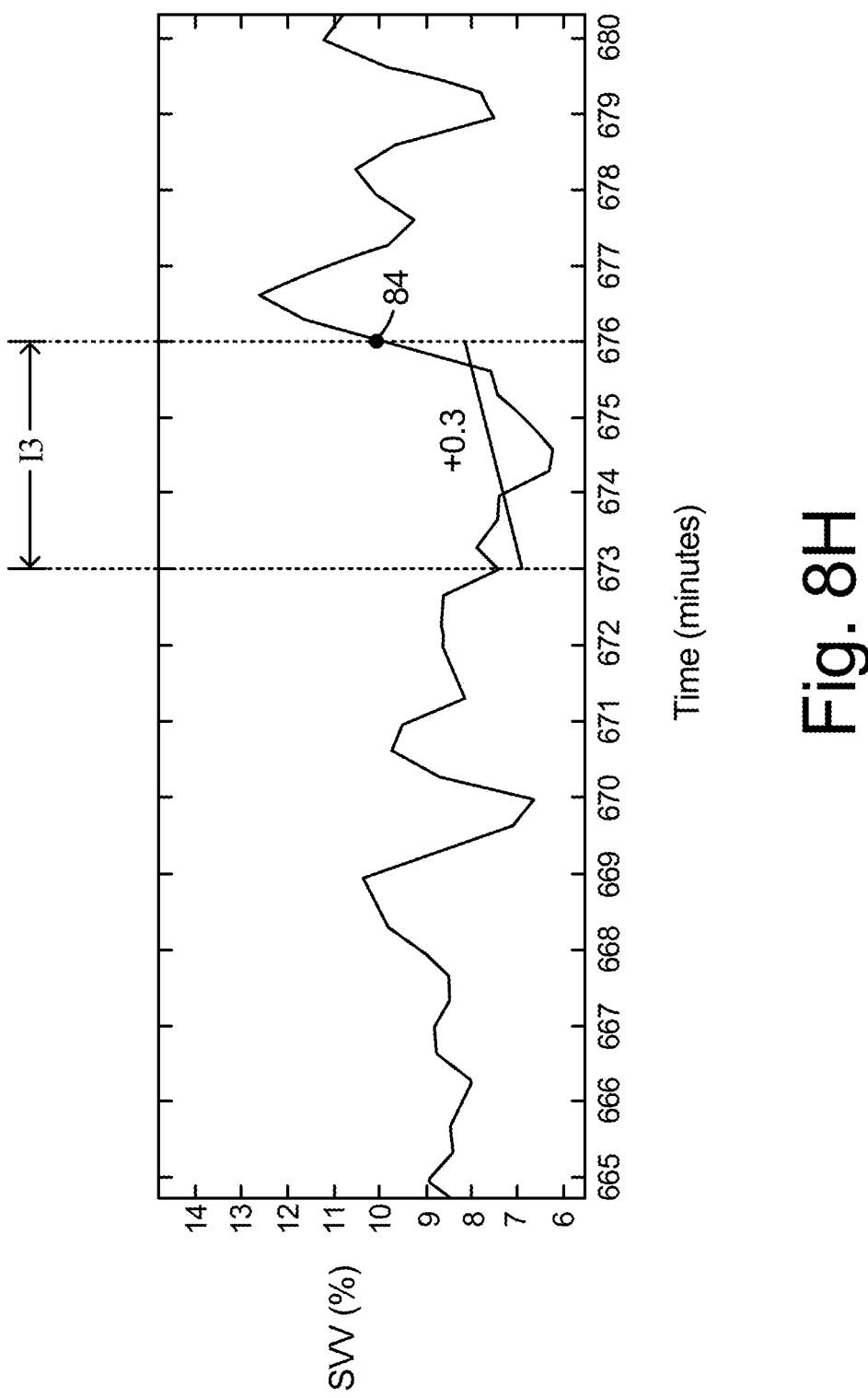
Figure 8I:
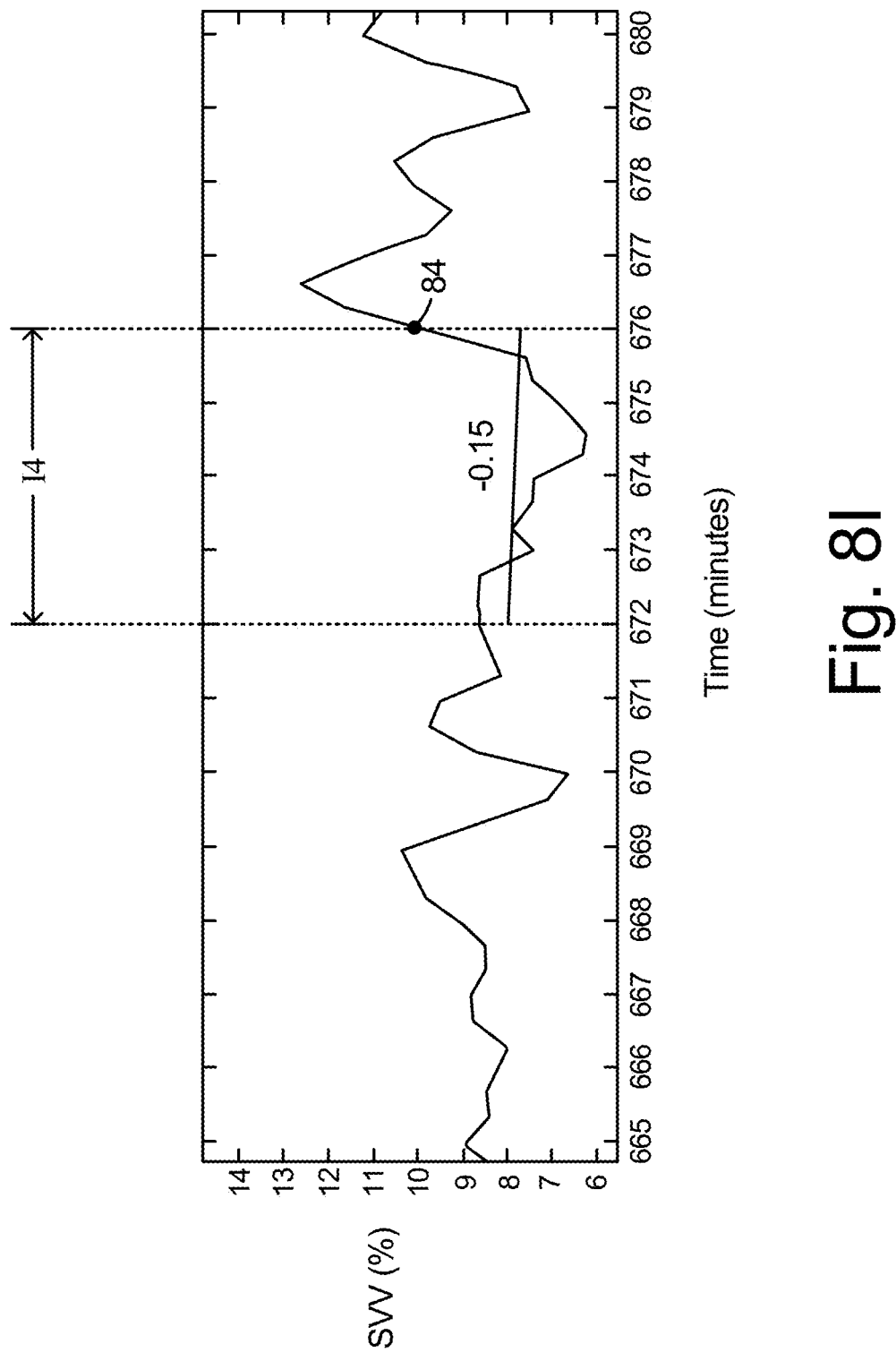
Figure 8J:
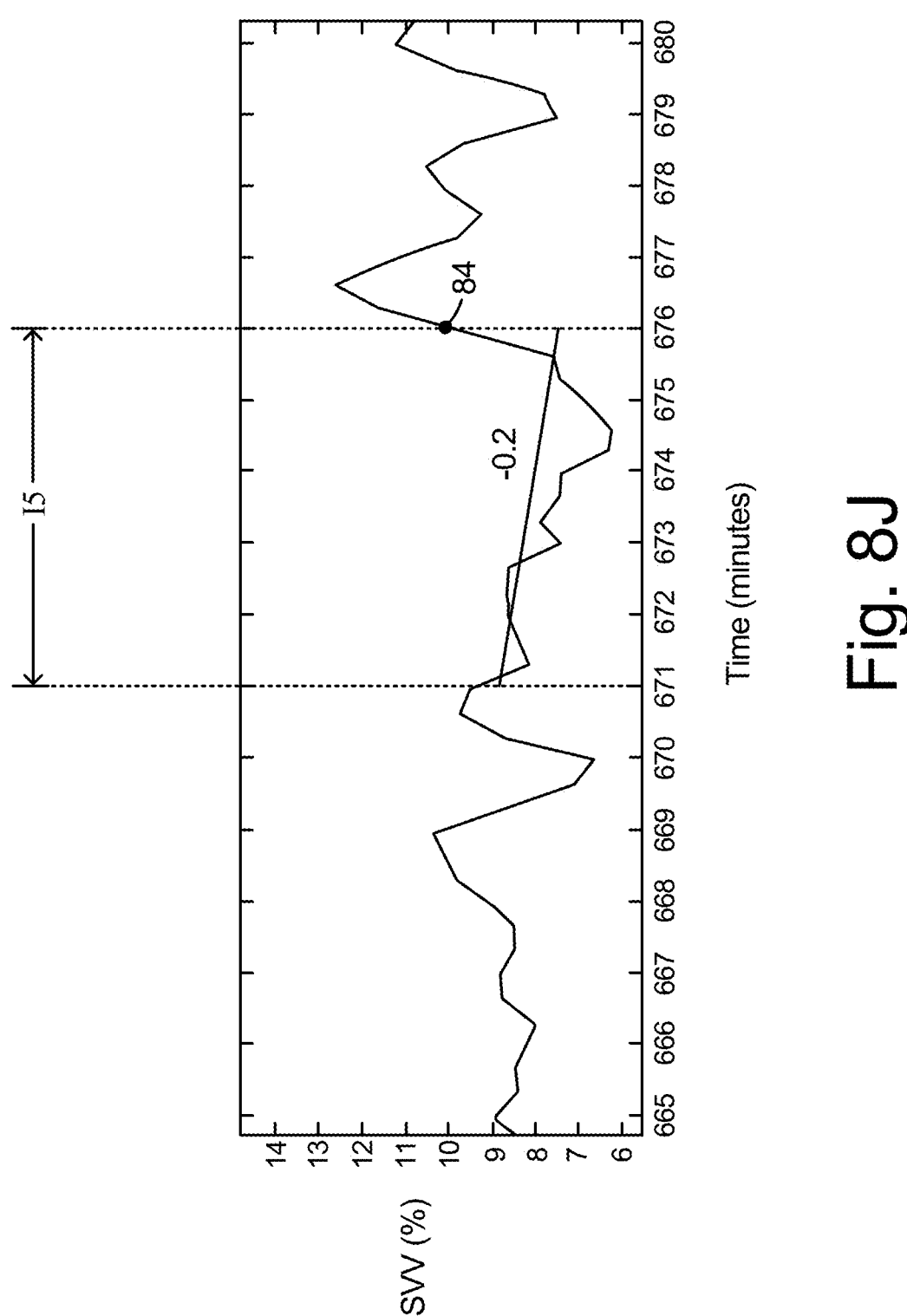

FIGS. 8G-8J illustrate examples of hemodynamic monitor 10 to determine the trend data of SVV for intervals I2-I5. For instance, in the example of FIG. 8G, hemodynamic monitor 10 determines a slope of a best-fit line through the SVV data included in interval 12 (i.e., SVV data from minute 674 to minute 676) as having a numerical value of positive 1.1. In FIG. 8H, hemodynamic monitor 10 determines a slope of a best-fit line through the SVV data included in interval 13 as having a numerical value of positive 0.3. In the example of FIG. 8I, hemodynamic monitor 10 determines a slope of a best-fit line through the SVV data included in interval 14 as having a numerical value of negative 0.15 (i.e., −0.15). In FIG. 8J, hemodynamic monitor 10 determines a slope of a best-fit line through the SVV data included in interval 15 as having a numerical value of negative 0.2 (i.e., −0.2).

FIG. 8K illustrates an example of hemodynamic monitor 10 to normalize the determined slope values associated with intervals I1-I5. As illustrated in FIG. 8K, hemodynamic monitor 10 can normalize each of the plurality of determined slope values to produce a plurality of normalized slope values ranging between, e.g., a numerical value of positive one (i.e., +1) and a numerical value of negative one (i.e., −1), though other normalized ranges are possible. In some examples, hemodynamic monitor 10 can normalize the plurality of determined slope values based on prior patient data. In other examples, hemodynamic monitor 10 can normalize the plurality of determined slope values based on a range of the determined slope values with respect to a range of the normalized values.

In the example of FIG. 8K, hemodynamic monitor 10 normalizes the determined slope of the best-fit line through the SVV data included in interval I1 as having a numerical value of positive one (i.e., +1). Hemodynamic monitor 10 normalizes the determined slope of the best-fit line through the SVV data included in interval 12 as having a numerical value of positive one (i.e., +1). Hemodynamic monitor 10 normalizes the determined slope of the best-fit line through the SVV data included in interval 13 as having a numerical value of positive 0.76 (i.e., 0.76). Hemodynamic monitor 10 normalizes the determined slope of the best-fit line through the SVV data included in interval 14 as having a numerical value of negative 0.34 (i.e., −0.34). Hemodynamic monitor 10 normalizes the determined slope of the best-fit line through the SVV data included in interval 15 as having a numerical value of negative 0.58 (i.e., −0.58).

Accordingly, hemodynamic monitor 10 can determine one or more normalized slopes of one or more best-fit lines of the hemodynamic parameter with respect to one or more corresponding defined time intervals. Hemodynamic monitor 10 utilizes the normalized slopes of the one or more best-fit lines for determining the trend score associated with the hemodynamic parameter.

FIG. 8L illustrates an example of hemodynamic monitor 10 to apply weighting factors to each of the normalized slopes of the best-fit lines of the SVV parameter data and to aggregate the weighted normalized slopes to determine a fluid trend sub-score. As illustrated in FIG. 8L, hemodynamic monitor 10 can apply a weighting factor to each of the normalized slopes of the best-fit lines, such as by multiplying each normalized slope by a corresponding weighting factor (illustrated in FIG. 8L as "Window Weights"). For instance, as illustrated in FIG. 8L, a weighting factor of 0.3 can be applied to the normalized slope value associated with interval I1 (i.e., a defined time interval including SVV data for a previous minute), a weighting factor of 0.2 can be applied to the normalized slope value associated with interval 12 (i.e., a defined time interval including SVV data for a previous two minutes), a weighting factor of 0.1 can be applied to the normalized slope value associated with interval 13 (i.e., a defined time interval including SVV data for a previous three minutes), a weighting factor of 0.05 can be applied to the normalized slope value associated with interval 14 (i.e., a defined time interval including SVV data for a previous four minutes), and a weighting factor of 0.02 can be applied to the normalized slope value associated with interval 15 (i.e., a defined time interval including SVV data for a previous five minutes).

It should be understood that the weighting factors described with respect to FIG. 8L are merely illustrative of example weighting factors, and that the values of such weighting factors can be different than those described with respect to the example of FIG. 8L. For example, the weighting factors applied by hemodynamic monitor 10 can be the same or different weighting factors, and can be determined, e.g., experimentally based on averaged (or otherwise aggregated) past patient data, such that the determined fluid trend sub-score aligns with effective clinical treatments with respect to known patient outcomes associated with the past patient data. In some examples, such as the example of FIG. 8L, normalized slope values associated with more recent time intervals can be weighted more heavily than normalized slope values associated with less recent time intervals.

As further illustrated in FIG. 8L, hemodynamic monitor 10 can aggregate the weighted normalized slope values according to, e.g., Equation 1 above. In the example of FIG. 8L, hemodynamic monitor 10 aggregates the weighted normalized slope values to produce an example fluid trend sub-score having a numerical value of 1.73.

Figure 8M:
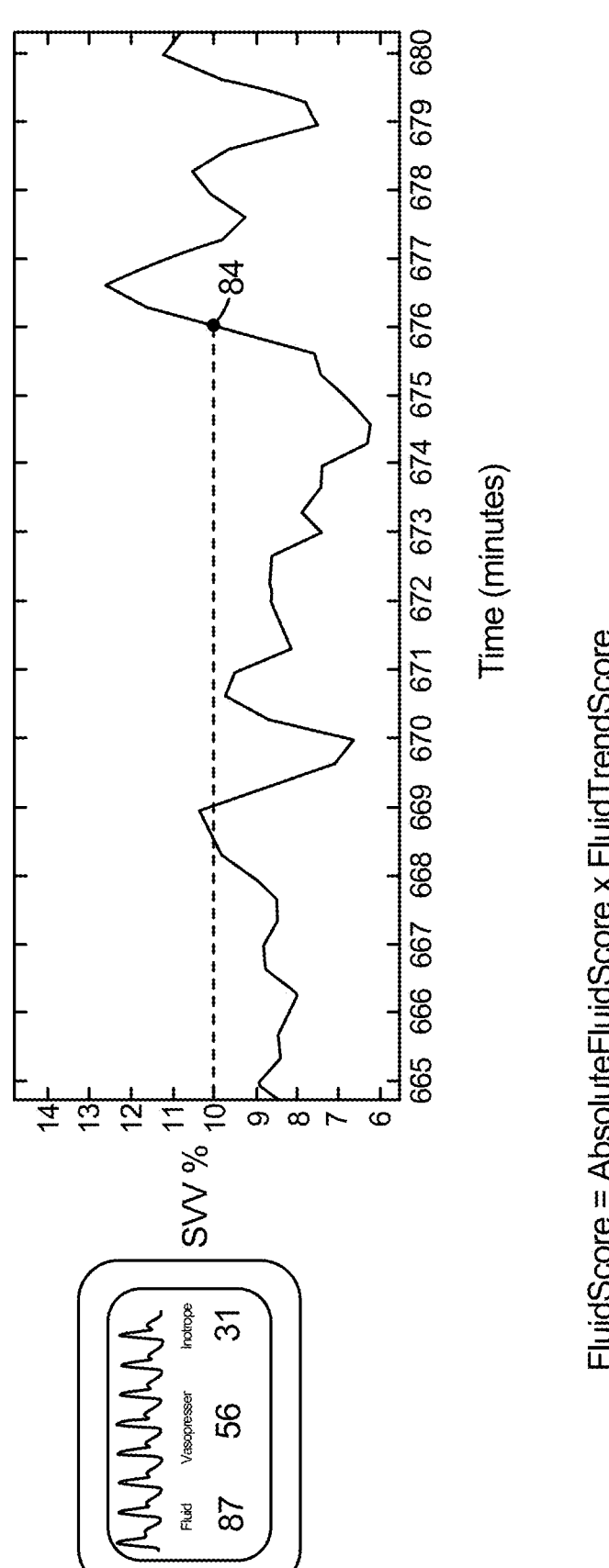
FIG. 8M is a chart illustrating an example for determining the fluid therapy score based on the magnitude sub-score and the trend sub-score.

FIG. 8M illustrates an example of hemodynamic monitor 10 to determine a fluid therapy score (illustrated in FIG. 8M as "FluidScore") as a combination of a fluid magnitude sub-score (illustrated in FIG. 8M as "AbsoluteFluidScore") and the fluid trend sub-score (illustrated in FIG. 8M as "FluidTrendScore"). In the example of FIG. 8M, hemodynamic monitor 10 determines the fluid magnitude sub-score, as described above with respect to FIG. 8B, as having a numerical value of 0.5 (i.e., based on a SVV value of 10% at initial evaluation point 84 and linearly interpolated between the lower magnitude threshold for the SVV parameter of 7% and the upper magnitude threshold for the SVV parameter of 13%).

Hemodynamic monitor 10 determines the fluid therapy score as the multiplicative product of the fluid magnitude sub-score and the fluid trend sub-score to produce the fluid therapy score having a numerical value of 0.865. In the example of FIG. 8M, hemodynamic monitor 10 outputs a representation of the fluid therapy score as a numerical value of 87, though in other examples, hemodynamic monitor 10 can output a different representation of the score. For instance, hemodynamic monitor 10 can output the raw score (e.g., a value of 0.867), a rounded raw score (e.g., a value of 0.87, a value of 0.9, or other rounded score), or other indication of the score. As was further described above, in certain examples, hemodynamic monitor 10 can output a representation of the score as a color-coded score, a symbolic representation of the score, or other representation that is indicative of the predicted responsiveness of the patient to the therapy represented by the score.

Accordingly, hemodynamic monitor 10, implementing techniques of this disclosure, can provide one or more scores that are predictive of responsiveness of a patient to a corresponding therapy to provide decision support to assist clinicians or other medical personnel with determinations of timely and effective therapeutic treatments for indicated hemodynamic conditions. As described above, though the examples of FIGS. 8A-8M are described with respect to the determination of a fluid therapy score that is predictive of responsiveness of a patient to the therapeutic delivery of fluids, the techniques of FIGS. 8A-8M are applicable to the determination of other therapy scores, such as a vasopressor therapy score that is predictive of responsiveness of the patient to therapeutic delivery of a vasopressor, and an inotrope therapy score that is predictive of responsiveness of the patient to therapeutic delivery of an inotrope.

FIG. 9A is a chart illustrating further examples for determining a magnitude sub-score associated with therapeutic intravenous delivery of fluid to the patient. As illustrated in FIG. 9A, hemodynamic monitor 10 can determine a magnitude sub-score associated with therapeutic delivery of fluids to the patient based on any one or more of SVV, PPV, SVI, and SV. For instance, as was similarly described above with respect to FIG. 8B, hemodynamic monitor 10 can determine the fluid magnitude sub-score (illustrated in FIG. 9A as "Fluid AbsoluteScore") as a normalized value based on the value of SVV.

As further illustrated in FIG. 9A, hemodynamic monitor 10 can determine the fluid magnitude sub-score as a normalized value based on the respective value of any one or more of PPV, SVI, and SV. For instance, as illustrated in FIG. 9A, hemodynamic monitor 10 can determine the fluid magnitude sub-score as a normalized value ranging between a lower normalized threshold having a numerical value of zero at a lower magnitude threshold of 7% PPV and an upper normalized threshold having a numerical value of one at an upper magnitude threshold of 13% PPV. Hemodynamic monitor 10 can determine the fluid magnitude sub-score as a normalized value ranging between a lower normalized threshold having a numerical value of zero at an upper magnitude threshold of 40 ml/m² SVI and an upper normalized threshold having a numerical value of one at a lower magnitude threshold of 30 ml/m² SVI. Hemodynamic monitor 10 can determine the fluid magnitude sub-score as a normalized value ranging between a lower normalized threshold having a numerical value of zero at an upper magnitude threshold of 80 ml SV and an upper normalized threshold having a numerical value of one at a lower magnitude threshold of 60 ml SV. As was similarly described above with respect to the example of FIG. 8B, the upper and lower normalized thresholds and the upper and lower magnitude thresholds described with respect to FIG. 9A are merely illustrative, and other normalized value thresholds and magnitude thresholds are possible.

FIG. 9B is a chart illustrating examples for determining a magnitude sub-score associated with therapeutic intravenous delivery of an inotrope to the patient. As was similarly described above with respect to FIGS. 8B and 9A (i.e., corresponding to the determination of a magnitude sub-score associated with therapeutic delivery of fluids to the patient), hemodynamic monitor 10 can determine the inotrope magnitude sub-score (illustrated in FIG. 9B as "Inotrope AbsoluteScore") as a normalized value based on a value of any one or more of $dP/dt_{max}$, CO, and CI. For instance, as illustrated in FIG. 9B, hemodynamic monitor 10 can determine the inotrope magnitude sub-score as a normalized value ranging between a lower normalized threshold having a numerical value of zero at an upper magnitude threshold of 700 mmHg/second $dP/dt_m$ax and an upper normalized threshold having a numerical value of one at a lower magnitude threshold of 400 mmHg/second $dP/dt_{max}$. Hemodynamic monitor 10 can determine the inotrope magnitude sub-score as a normalized value ranging between a lower normalized threshold having a numerical value of zero at an upper magnitude threshold of 6 L/minute CO and an upper normalized threshold having a numerical value of one at a lower magnitude threshold of 4 L/minute CO. Hemodynamic monitor 10 can determine the inotrope magnitude sub-score as a normalized value ranging between a lower normalized threshold having a numerical value of zero at an upper magnitude threshold of 3 L/minute/m² CI and an upper normalized threshold having a numerical value of one at a lower magnitude threshold of 2 L/minute/m² CI. It should be understood that the upper and lower normalized thresholds and the upper and lower magnitude thresholds described with respect to FIG. 9B are merely illustrative, and other normalized value thresholds and magnitude thresholds are possible.

FIG. 9C is a chart illustrating examples for determining a magnitude sub-score associated with therapeutic intravenous delivery of a vasopressor to the patient. As was similarly described above, hemodynamic monitor 10 can determine the vasopressor magnitude sub-score (illustrated in FIG. 9C as "Vasopressor AbsoluteScore") as a normalized value based on a value of any one or more of SVR and SVRI. For instance, hemodynamic monitor 10 can determine the vasopressor magnitude sub-score as a normalized value ranging between a lower normalized threshold having a numerical value of zero at an upper magnitude threshold of 1100 dynes·sec·cm$^5$ SVR and an upper normalized threshold having a numerical value of one at a lower magnitude threshold of 88 mmHg SVR. Hemodynamic monitor 10 can determine the vasopressor magnitude sub-score as a normalized value ranging between a lower normalized threshold having a numerical value of zero at an upper magnitude threshold of 2200 dynes·sec·cm$^{-5}$·m$^2$ SVRI and an upper normalized threshold having a numerical value of one at a lower magnitude threshold of 1600 dynes·sec·cm$^{-5}$·m$^2$ SVRI.

As was similarly described with respect to a fluid therapy score in the examples of FIGS. 8A-8M, hemodynamic monitor 10 can determine one or more of a vasopressor therapy score and an inotrope therapy score using the vasopressor magnitude sub-score and the inotrope magnitude sub-score. For example, hemodynamic monitor 10 can determine a vasopressor trend sub-score based on trend data derived from SVR parameter data (or SVRI parameter data) of the patient to produce a vasopressor therapy as a combination of the vasopressor magnitude sub-score and the vasopressor trend sub-score. Hemodynamic monitor 10 can determine an inotrope trend sub-score based on trend data derived from dP/dt$_{max}$ parameter data (or CO parameter data, or CI parameter data) of the patient to produce an inotrope therapy score as a combination of the inotrope magnitude sub-score and the inotrope trend sub-score.

Accordingly, as described herein, a hemodynamic monitor can provide one or more scores that are predictive of responsiveness of a patient to a corresponding therapy, thereby reducing the information processing burden on attending medical personnel and providing decision support to such medical personnel for timely and effective delivery of therapeutic treatments for indicated hemodynamic conditions. The provided scores, which are determined from not only magnitude data but also from trend data of the derived hemodynamic parameters, can help to indicate the future responsiveness of the patient to the corresponding therapy, thereby further enhancing the decision support provided by the corresponding scores.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A system for monitoring arterial pressure of a patient and determining one or more scores that are predictive of responsiveness of the patient to a corresponding therapy, the system comprising:
   a hemodynamic sensor that produces sensed hemodynamic data representative of an arterial pressure waveform of the patient;

a system memory that stores hemodynamic therapy scoring software code;
   a user interface; and
   a hardware processor that is configured to execute the hemodynamic therapy scoring software code to:
      derive, from the sensed hemodynamic data representative of the arterial pressure waveform of the patient, first magnitude data and first trend data of a first hemodynamic parameter selected from the group consisting of a stroke volume variation (SVV), a pulse pressure variation (PPV), a stroke volume (SV), and a stroke volume index (SVI), wherein the first hemodynamic parameter is indicative of a condition treatable by an intravenous delivery of a saline fluid to the patient;
      derive, from the sensed hemodynamic data representative of the arterial pressure waveform of the patient, second magnitude data and second trend data of a second hemodynamic parameter selected from the group consisting of a systemic vascular resistance (SVR) and a systemic vascular resistance index (SVRI), wherein the second hemodynamic parameter is indicative of a condition treatable by an intravenous delivery of a vasopressor to the patient;
      derive, from the sensed hemodynamic data representative of the arterial pressure waveform of the patient, third magnitude data and third trend data of a third hemodynamic parameter selected from the group consisting of a maximal rate of rise of arterial pressure (dP/dt$_{max}$), a cardiac output (CO), and a cardiac index (CI), wherein the third hemodynamic parameter is indicative of a condition treatable by an intravenous delivery of an inotrope to the patient;
      determine a first magnitude sub-score based on the first magnitude data, a second magnitude sub-score based on the second magnitude data, and a third magnitude sub-score based on the third magnitude data;
      determine a first trend sub-score based on the first trend data, a second trend sub-score based on the second trend data, and a third trend sub-score based on the third trend data;
      determine a first score as a combination of the first magnitude sub-score and the first trend sub-score, a second score as a combination of the second magnitude sub-score and the second trend sub-score, and a third score as a combination of the third magnitude sub-score and the third trend sub-score; and
      output, via the user interface, a representation of the first score that is predictive of responsiveness of the patient to the intravenous delivery of the saline fluid, a representation of the second score that is predictive of responsiveness of the patient to the intravenous delivery of the vasopressor, and a representation of the third score that is predictive of responsiveness of the patient to the intravenous delivery of the inotrope.

2. The system of claim 1, wherein the hardware processor is configured to execute the hemodynamic therapy scoring software code to determine the first score as the combination of the first magnitude sub-score and the first trend sub-score by determining the first score as a multiplicative product of the first magnitude sub-score and the first trend sub-score.

3. The system of claim 1, wherein the hardware processor is configured to execute the hemodynamic therapy scoring software code to determine the first magnitude sub-score as a normalized value ranging between a lower normalized threshold at a lower magnitude threshold of the first magnitude data of the first hemodynamic parameter and an upper normalized threshold at an upper magnitude threshold of the first magnitude data of the first hemodynamic parameter.

4. The system of claim 1, wherein the hardware processor is configured to execute the hemodynamic therapy scoring software code to derive the first trend data of the first hemodynamic parameter by determining a slope of a best-fit line of the first hemodynamic parameter associated with a defined time interval.

5. The system of claim 4, wherein the hardware processor is configured to execute the hemodynamic therapy scoring software code to determine the first trend sub-score by normalizing the slope of the best-fit line of the first hemodynamic parameter to determine a normalized slope of the best-fit line of the first hemodynamic parameter associated with the defined time interval.

6. The system of claim 5, wherein the hardware processor is configured to execute the hemodynamic therapy scoring software code to determine the first trend sub-score by applying a weighting factor to the normalized slope of the best-fit line of the first hemodynamic parameter to determine a weighted normalized slope of the best-fit line of the first hemodynamic parameter associated with the defined time interval.

7. The system of claim 1, wherein the hardware processor is configured to execute the hemodynamic therapy scoring software code to derive the first trend data of the first hemodynamic parameter by determining a plurality of slopes of a plurality of best-fit lines of the first hemodynamic parameter associated with a plurality of defined time intervals.

8. The system of claim 1, wherein the hardware processor is configured to execute the hemodynamic therapy scoring software code to determine the second score as the combination of the second magnitude sub-score and the second trend sub-score by determining the second score as a multiplicative product of the second magnitude sub-score and the second trend sub-score.

9. The system of claim 1, wherein the hardware processor is configured to execute the hemodynamic therapy scoring software code to determine the second magnitude sub-score as a normalized value ranging between a lower normalized threshold at a lower magnitude threshold of the second magnitude data of the second hemodynamic parameter and an upper normalized threshold at an upper magnitude threshold of the second magnitude data of the second hemodynamic parameter.

10. The system of claim 1, wherein the hardware processor is configured to execute the hemodynamic therapy scoring software code to derive the second trend data of the second hemodynamic parameter by determining a slope of a best-fit line of one or more best-fit lines of the second hemodynamic parameter associated with a defined time interval.

11. The system of claim 1, wherein the hardware processor is configured to execute the hemodynamic therapy scoring software code to derive the second trend data of the second hemodynamic parameter by determining a plurality of slopes of a plurality of best-fit lines of the second hemodynamic parameter associated with a plurality of defined time intervals.

12. The system of claim 1, wherein the hardware processor is configured to execute the hemodynamic therapy scoring software code to determine the third score as the combination of the third magnitude sub-score and the third trend sub-score by determining the third score as a multiplicative product of the third magnitude sub-score and the third trend sub-score.

13. The system of claim 1, wherein the hardware processor is configured to execute the hemodynamic therapy scoring software code to determine the third magnitude sub-score as a normalized value ranging between a lower normalized threshold at a lower magnitude threshold of the third magnitude data of the third hemodynamic parameter and an upper normalized threshold at an upper magnitude threshold of the third magnitude data of the third hemodynamic parameter.

14. The system of claim 1, wherein the hardware processor is configured to execute the hemodynamic therapy scoring software code to derive the third trend data of the third hemodynamic parameter by determining a slope of a best-fit line of one or more best-fit lines of the third hemodynamic parameter associated with a defined time interval.

15. The system of claim 1, wherein the hardware processor is configured to execute the hemodynamic therapy scoring software code to derive the third trend data of the third hemodynamic parameter by determining a plurality of slopes of a plurality of best-fit lines of the third hemodynamic parameter associated with a plurality of defined time intervals.

16. The system of claim 1, wherein:

the first trend data of the first hemodynamic parameter is based on one or more first best fit lines, the second trend data of the second hemodynamic parameter is based on one or more second best fit lines, and the third trend data of the third hemodynamic parameter is based on one or more third best fit lines; and the one or more first best fit lines, the one or more second best fit lines, and the one or more third best fit lines are determined using linear regression.

17. A system for monitoring arterial pressure of a patient and determining one or more scores that are predictive of responsiveness of the patient to a corresponding therapy, the system comprising:

a hemodynamic sensor that produces sensed hemodynamic data representative of an arterial pressure waveform of the patient;

a system memory that stores hemodynamic therapy scoring software code;

a user interface; and a hardware processor that is configured to execute the hemodynamic therapy scoring software code to:

derive, from the sensed hemodynamic data representative of the arterial pressure waveform of the patient:

first magnitude data and first trend data of a first hemodynamic parameter indicative of a condition treatable by an intravenous delivery of a saline fluid to the patient;

second magnitude data and second trend data of a second hemodynamic parameter indicative of a condition treatable by an intravenous delivery of a vasopressor to the patient; and third magnitude data and third trend data of a third hemodynamic parameter indicative of a condition treatable by an intravenous delivery of an inotrope to the patient;

wherein the first hemodynamic parameter, the second hemodynamic parameter, and the third hemodynamic parameter are different from one another;

determine a first magnitude sub-score based on the first magnitude data, a second magnitude sub-score based on the second magnitude data, and a third magnitude sub-score based on the third magnitude data;

determine a first trend sub-score based on the first trend data, a second trend sub-score based on the second trend data, and a third trend sub-score based on the third trend data;

determine a first score as a combination of the first magnitude sub-score and the first trend sub-score, a second score as a combination of the second magnitude sub-score and the second trend sub-score, and a third score as a combination of the third magnitude sub-score and the third trend sub-score; and output, via the user interface, a representation of the first score that is predictive of responsiveness of the patient to the intravenous delivery of the saline fluid, a representation of the second score that is predictive of responsiveness of the patient to the intravenous delivery of the vasopressor, and a representation of the third score that is predictive of responsiveness of the patient to the intravenous delivery of the ino-trope.

18. The system of claim 17, wherein the first hemodynamic parameter is selected from the group consisting of a stroke volume variation (SVV), a pulse pressure variation (PPV), a stroke volume (SV), and a stroke volume index (SVI).

19. The system of claim 17, wherein the second hemodynamic parameter is selected from the group consisting of a systemic vascular resistance (SVR) and a systemic vascular resistance index (SVRI).

20. The system of claim 17, wherein the third hemodynamic parameter is selected from the group consisting of a maximal rate of rise of arterial pressure ($dP/dt_{max}$), a cardiac output (CO), and a cardiac index (CI).

*   *   *   *   *